(12) United States Patent
Urakawa et al.

(10) Patent No.: US 11,603,342 B2
(45) Date of Patent: Mar. 14, 2023

(54) METHANOL PRODUCTION PROCESS

(71) Applicant: FUNDACIÓ INSTITUT CATALÀ D'INVESTIGACIÓ QUÍMICA (ICIQ), Tarragona (ES)

(72) Inventors: Atsushi Urakawa, Fukuoka (JP); Atul Bansode, Maharashtra (IN); Rohit Vilas Gaikwad, Maharashtra (IN)

(73) Assignee: FUNDACIÓ INSTITUT CAT ALÁ DINVESTIGACIÓ QUÍMICA (ICIQ), Tarragona (ES)

( * ) Notice: Subject to any disclaimer, the term of this patent is extended or adjusted under 35 U.S.C. 154(b) by 102 days.

(21) Appl. No.: 15/998,895

(22) PCT Filed: Feb. 16, 2017

(86) PCT No.: PCT/EP2017/053535
§ 371 (c)(1),
(2) Date: Aug. 16, 2018

(87) PCT Pub. No.: WO2017/140800
PCT Pub. Date: Aug. 24, 2017

(65) Prior Publication Data
US 2020/0207689 A1    Jul. 2, 2020

(30) Foreign Application Priority Data

Feb. 16, 2016   (EP) .................................. 16382062

(51) Int. Cl.
| | | |
|---|---|---|
| *C07C 29/154* | (2006.01) | |
| *B01J 23/06* | (2006.01) | |
| *B01J 23/72* | (2006.01) | |
| *B01J 35/02* | (2006.01) | |
| *B01J 35/10* | (2006.01) | |
| *C07C 31/04* | (2006.01) | |

(52) U.S. Cl.
CPC ............ *C07C 29/154* (2013.01); *B01J 23/06* (2013.01); *B01J 23/72* (2013.01); *B01J 35/023* (2013.01); *B01J 35/1014* (2013.01); *C07C 31/04* (2013.01)

(58) Field of Classification Search
None
See application file for complete search history.

(56) References Cited

U.S. PATENT DOCUMENTS

| | | | |
|---|---|---|---|
| 1,558,559 A | 10/1925 | Mittasch et al. | |
| 1,569,775 A | 1/1926 | Mittasch et al. | |
| 3,326,956 A * | 6/1967 | Davies et al. | C07C 29/154 518/713 |
| 3,689,575 A * | 9/1972 | Tarhan | C07C 29/159 568/840 |
| 3,897,471 A * | 7/1975 | Herbert | C07C 31/04 518/713 |
| 3,923,694 A * | 12/1975 | Cornthwaite | B01J 23/72 502/342 |
| 3,939,191 A * | 2/1976 | Asano | B01J 23/80 518/713 |
| 4,126,581 A | 11/1978 | Sugier et al. | |
| 4,181,630 A * | 1/1980 | Baglin | B01J 23/72 252/373 |
| 4,226,795 A * | 10/1980 | Bowman | C07C 29/1512 518/704 |
| 4,279,781 A * | 7/1981 | Dienes | B01J 23/80 502/343 |
| 4,477,594 A | 10/1984 | Greene et al. | |
| 4,623,668 A * | 11/1986 | Broecker | C07C 29/154 502/38 |
| 4,639,470 A * | 1/1987 | Mednick | C07C 29/1512 518/700 |
| 4,788,175 A * | 11/1988 | Short | C07C 29/154 502/342 |
| 6,342,538 B1 * | 1/2002 | Matsumura | B01J 23/63 518/700 |
| 7,579,383 B2 * | 8/2009 | Lattner | C07C 29/1512 518/700 |
| 8,439,991 B2 * | 5/2013 | Abbott | C10K 3/04 48/61 |

(Continued)

FOREIGN PATENT DOCUMENTS

| | | |
|---|---|---|
| CN | 1112912 A | 12/1995 |
| CN | 102516029 A | 6/2012 |

(Continued)

OTHER PUBLICATIONS

M. Saito et al., 138 Applied Catalysis A: General, 311-318 (1993) (Year: 1993).*
Y. Amenomiya et al., 30 Applied Catalysis, 57-68 (1987) (Year: 1987).*
M. McNeil et al., 50 Applied Catalysis, 265-285 (1989) (Year: 1989).*
C. Schack et al., 50 Applied Catalysis, 247-263 (1989) (Year: 1989).*
R. Gaikwad et al., 343 Journal of Catalysis, 127-132 (2016) (Year: 2016).*

(Continued)

*Primary Examiner* — Alexander R Pagano
(74) *Attorney, Agent, or Firm* — Hayes Soloway PC

(57) ABSTRACT

The invention provides a process for producing methanol, which process comprises contacting $H_2$ and $CO_2$ with a solid catalyst, at a temperature of from 200° C. to 300° C. and at a reactant pressure of from 150 bar to 500 bar, which reactant pressure is the sum of the partial pressures of the $H_2$ and the $CO_2$, wherein: the molar ratio of the $H_2$ to the $CO_2$ is x:1.0, wherein x is from 2.5 to 3.5; and the catalyst comprises: (i) a copper component which is Cu, CuO or $Cu_2O$, or a mixture of two or three thereof, and (ii) ZnO, wherein the catalyst has a specific copper surface area of at least 10 $m^2$/g-catalyst.

4 Claims, 4 Drawing Sheets

(56) References Cited

U.S. PATENT DOCUMENTS

| | | | |
|---|---|---|---|
| 8,957,117 B2* | 2/2015 | Park | C07C 29/154 |
| | | | 518/714 |
| 9,133,074 B2* | 9/2015 | Jennings | C07C 29/151 |
| 9,133,084 B2* | 9/2015 | Urakawa | B01J 35/0006 |
| 9,492,809 B2* | 11/2016 | Park | C01B 3/16 |
| 10,252,963 B2* | 4/2019 | Kambe | B01J 23/80 |
| 10,550,055 B2* | 2/2020 | Modarresi | B01J 8/0457 |
| 2010/0088951 A1 | 4/2010 | White et al. | |
| 2011/0136924 A1* | 6/2011 | Fujimoto | B01J 23/80 |
| | | | 518/700 |
| 2015/0133699 A1* | 5/2015 | Urakawa | C07C 29/1512 |
| | | | 568/840 |
| 2017/0121259 A1* | 5/2017 | Kurr | B01J 35/023 |
| 2018/0362426 A1* | 12/2018 | Chen | B01J 23/80 |

FOREIGN PATENT DOCUMENTS

| | | | |
|---|---|---|---|
| CN | 104039444 A | 9/2014 | |
| DE | 415686 C | 6/1925 | |
| DE | 141433 C | 3/1927 | |
| DE | 462837 C | 7/1928 | |
| JP | 2015-502248 A | 1/2015 | |
| JP | 2015-054312 A | 3/2015 | |
| WO | WO-2013054092 A1* | 4/2013 | B01J 37/03 |
| WO | WO/2013/072197 A1 | 5/2013 | |
| WO | WO/2013/171239 A1 | 11/2013 | |
| WO | WO-2013171239 A1* | 11/2013 | B01J 37/031 |

OTHER PUBLICATIONS

PP. Tijm et al., 221 Applied Catalysis A: General, 275-282 (2001) (Year: 2001).*

I. Kasatkin et al., 46 Angew. Chem. Int. Ed., 7324-7327 (2007) (Year: 2007).*

H. Ren et al., 28 Journal of Industrial and Engineering Chemistry, 261-267 (2015) (Year: 2015).*

S. Zander et al., 52 Angew. Chem. Int. Ed., 6536-6540 (2013) (Year: 2013).*

Search Report issued in Russian Application No. 2018132745 dated Mar. 31, 2020, Mar. 31, 2020.

An, et al., "Methanol Synthesis from $CO_2$ Hydrogenation with a Cu/Zn/Al/Zr Fibrous Catalyst", Chinese Journal of Chemical Engineering, vol. 17, No. 1, Mar. 5, 2009, 88-94.

Sazonov, "Methanol Synthesis Catalysts", Letters of Higher Educational Institutions. Oil and Gas, No. 2, 2010, 117-122.

Atul Bansode, et al.: "Towards full one-pass conversion of carbon dioxide to methanol and methanol-derived products", Journal of Catalysis., vol. 309, Oct. 8, 2013 (2013-10-08), pp. 66-70.

Atul Bansode, et al.: "Supplementary Material Towards full one-pass conversion of carbon dioxide to methanol and methanol-derived products", Jan. 1, 2014 (Jan. 1, 2014).

Bansode, et al., "Impact of K and Ba promoters on $CO_2$ hydrogenation over $Cu/Al_2O_3$, catalysts at high pressure", Catalysis Science & Technology, vol. 9 Issue 3, Dec. 6, 2012, 767-778.

Dumesic, et al., "Principles of Heterogeneous Catalysis", Handbook of Heterogeneous Catalysis, Mar. 15, 2008, 1-15.

Evans, et al., Applied Catalysis, vol. 7 Issue 1, Jul. 15, 1983, 75-83.

Gaikwad, et al., "High-pressure advantages in stoichiometric hydrogenation of carbon dioxide to methanol", Journal of Catalysis, vol. 343, Feb. 24, 2016, 127-132.

Hansen, et al., "Methanol Synthesis", Handbook of Heterogeneous Catalysis, Mar. 15, 2008, 2920-2949.

Ipatieff, et al., "Synthesis of Methanol from Carbon Dioxide and Hydrogen over Copper-Alumina Catalysts. Mechanism of Reaction", Journal of the American Chemical Society, vol. 67 Issue 12, Dec. 1, 1945, 2168-2171.

Kunkes, et al., "Hydrogenation of $CO_2$ to methanol and CO on $Cu/ZnO/Al_2O_3$, Is there a common intermediate or not?", Journal of Catalysis, vol. 328, Jun. 5, 2015, 43-48.

Lok, "Coprecipitation", Synthesis of Solid Catalysts, Oct. 1, 2009, 135-151.

Mikkelsen, et al., "The teraton challenge. A review of fixation and transformation of carbon dioxide", Energy & Environmental Science, vol. 3 Issue 1, Nov. 24, 2009, 43-81.

Nowick, "X-ray diffraction procedures for polycrystalline and amorphous materials. H. P. Klug and L. E. Alexander. John Wiley and Sons, Inc., New York (1954). 716 pages. $15.00", AIChE Journal, vol. 2 Issue 1, Mar. 1, 1956, 140.

Olah, "Beyond Oil and Gas: The Methanol Economy", Angewandte Chemie International Edition, vol. 44 Issue 18, Mar. 31, 2005, 2636-2639.

Pontzen, et al., "$CO_2$-based methanol and DME—Efficient technologies for industrial scale production", Catalysis Today, vol. 171 Issue 1, Jul. 2, 2011, 242-250.

Queiroz F. Araújo, et al., "$CO_2$ Utilization: A Process Systems Engineering Vision", $CO_2$ Sequestration and Valorization, Mar. 12, 2014, 35-88.

Skrzypek, et al., "Thermodynamics and kinetics of low pressure methanol synthesis", The Chemical Engineering Journal, vol. 58 Issue 2, Jun. 1, 1995, 101-108.

Tidona, et al., "$CO_2$ hydrogenation to methanol at pressures up to 950 bar", The Journal of Supercritical Fluids, vol. 78 Issue, Jun. 1, 2013, 70-77.

Van Bennekom, et al., "Methanol synthesis beyond chemical equilibrium", Chemical Engineering Science, vol. 87, Oct. 16, 2012, 204-208.

Van Bennekom, et al., "Modeling and Experimental Studies on Phase and Chemical Equilibria in High-Pressure Methanol Synthesis", Industrial & Engineering Chemistry Research, vol. 51 Issue 38, Aug. 27, 2012, 12,233-12,243.

Zhao, et al., "A novel low-temperature methanol synthesis method from $CO/H_2/CO_2$ based on the synergistic effect between solid catalyst and homogeneous catalyst", Catalysis Today, vol. 149 Issues 1-2, Aug. 18, 2009, 98-104.

* cited by examiner

METHANOL PRODUCTION PROCESS

FIELD OF THE INVENTION

The invention relates to a process for producing methanol.

BACKGROUND TO THE INVENTION

The ever-increasing energy demand to sustain industrialization and modern lifestyle has led to depletion consumption of the world's current primary energy supply, finite and non-renewable fossil fuels. In parallel, their irreversible consumption has resulted in accumulation of carbon dioxide ($CO_2$) in the atmosphere, causing the climate to change. For sustainable development of mankind, the carbon cycle has to be closed; conversion of $CO_2$ into chemical fuels and feedstocks serves as an effective strategy to cope with the interrelated energetic and environmental problems (M. Mikkelsen, M. Jorgensen, F. C. Krebs, Energ. Environ. Sci., 3 (2010) 43-81). Heterogeneous catalytic conversion of $CO_2$ to fuels and industrially important chemicals, such as methanol, by the hydrogenation reaction, offers a unique path to transform a large amount of $CO_2$ in a short span of time by high reaction rates. The vital roles of methanol as a chemical energy carrier and starting material or as a chemical intermediate are well recognized (G. A. Olah, Angew. Chem. Int. Ed., 44 (2005) 2636-2639). However, $CO_2$ is a thermodynamically stable and relatively inert molecule. Its activation typically requires energy input, e.g. by the use of elevated pressure and temperature as well as effectual strategies such as innovative catalytic processes (O. d. Q. F. Araujo, J. L. d. Medeiros, R. M. B. Alves, $CO_2$ Utilization: A Process Systems Engineering Vision, 2014; A. Bansode, B. Tidona, P. R. von Rohr, A. Urakawa, Catal. Sci. Technol., 3 (2013) 767-778; V. N. Ipatieff, G. S. Monroe, J. Am. Chem. Soc., 67 (1945) 2168-2171; J. G. van Bennekom, R. H. Venderbosch, J. G. M. Winkelman, E. Wilbers, D. Assink, K. P. J. Lemmens, H. J. Heeres, Chem. Eng. Sci., 87 (2013) 204-208).

$CO_2$ hydrogenation to methanol is exothermic (reaction 1), while the competing reaction, reverse water-gas shift (RWGS, reaction 2), is endothermic (J. A. Dumesic, G. W. Huber, M. Boudart, Principles of Heterogeneous Catalysis, in: Handbook of Heterogeneous Catalysis, Wiley-VCH Verlag GmbH & Co. KGaA, 2008). Moreover, CO produced by RWGS may undergo exothermic hydrogenation to form methanol (reaction 3).

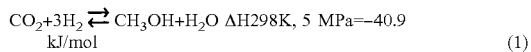

$$CO_2 + 3H_2 \rightleftarrows CH_3OH + H_2O \quad \Delta H298K, 5\ MPa = -40.9\ kJ/mol \quad (1)$$

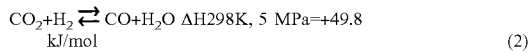

$$CO_2 + H_2 \rightleftarrows CO + H_2O \quad \Delta H298K, 5\ MPa = +49.8\ kJ/mol \quad (2)$$

$$CO + 2H_2 \rightleftarrows CH_3OH \quad \Delta H298K, 5MPa = -90.7\ kJ/mol \quad (3)$$

In accordance with Le Châtelier's principle, high-pressure and low-temperature reaction conditions are favorable to achieve high $CO_2$ conversion and methanol selectivity (J. Skrzypek, M. Lachowska, M. Grzesik, J. Sloczyfiski, P. Nowak, Chem. Eng. J. and Biochem. Eng. J., 58 (1995) 101-108). In fact, the advantage and necessity of high-pressure conditions in the synthesis of methanol from syngas (CO and $H_2$ mixture typically containing some fraction of $CO_2$) has been known for the last 90 years (BASF, German Patent nos. 415 686, 441 433, and 462 837, 1923).

Since 1966, the trend has shifted to lower pressure methanol synthesis (<100 bar) using highly active and economic Cu—ZnO based catalysts (J. B. Hansen, P. E. Højlund Nielsen, Methanol Synthesis, in: Handbook of Heterogeneous Catalysis, Wiley-VCH Verlag GmbH & Co. KGaA, 2008). For this family of catalysts which are the most common for methanol synthesis nowadays, high-pressure advantages in methanol synthesis by the hydrogenation of CO and particularly $CO_2$ had not been explored and documented for a long time, except in the work reported by Ipatieff and Monroe in 1945 for Cu-based catalysts (V. N. Ipatieff, G. S. Monroe, J. Am. Chem. Soc., 67 (1945) 2168-2171).

Recently, a range of high-pressure reaction conditions was reported to yield almost-full one-pass conversion of $CO_2$ to methanol with high selectivity using $Cu/ZnO/Al_2O_3$ catalysts and also to methanol-derived products such as dimethyl ether (DME) by co-adding an acidic zeolite (A. Bansode, A. Urakawa, J. Catal., 309 (2014) 66-70 and WO 2013/171239 A1). An elevated $H_2$ partial pressure (a molar ratio of $CO_2$:$H_2$=1:>10), higher than that at the stoichiometric ratio (i.e. $CO_2$:$H_2$=1:3, by reaction 1), was reported to be kinetically as well as thermodynamically beneficial for methanol synthesis. Employing a reaction pressure of 360 bar (equating to a reactant pressure of 331 bar, due to the presence of Ar for GC analysis) was reported to achieve outstanding $CO_2$ conversion (>95%) and methanol selectivity (>98%), at 260° C. and at a relatively high gas hourly space velocity (GHSV) of ca. 10,000 $h^{-1}$. The catalyst employed to achieve this was a $Cu/ZnO/Al_2O_3$ catalyst, which is referred to in J. Catal., 309 (2014) 66-70 as "$Cu/ZnO/Al_2O_3$(I)". The same catalyst is also employed in many of the reactions described in WO 2013/171239 A1, and is referred to in that document as mixture (IIA). Energy-demanding high-pressure conditions are not necessarily disadvantageous in this reaction because of smaller geometrical requirements for the reactor and plant area, which lowers the capital cost and possibly improve safety aspects (A. Bansode, B. Tidona, P. R. von Rohr, A. Urakawa, Catal. Sci. Technol., 3 (2013) 767-778; A. Bansode, A. Urakawa, J. Catal., 309 (2014) 66-70). Moreover, the energetic cost associated with compression of the reactants is less significant than that required for hydrogen production in the overall process of $CO_2$ hydrogenation to methanol (B. Tidona, C. Koppold, A. Bansode, A. Urakawa, P. Rudolf von Rohr, J. Supercrit. Fluids, 78 (2013) 70-77). However, despite the exceptionally high $CO_2$ conversion and methanol selectivity under high-pressure conditions and also high process viability in terms of costs and methanol productivity, the reported reaction condition requires recycling or further conversion of unreacted $H_2$ fed in excess. In addition, the CO produced by RWGS needs to be recycled if methanol selectivity is not sufficiently high.

Recycling of precious $H_2$ can only be avoided by achieving its full conversion. In other words, the challenge in this respect is to achieve complete conversion of both $CO_2$ and $H_2$ with high methanol productivity, leaving little or no CO in the product stream.

This goal would require the operation of the reaction at or close to the stoichiometric $CO_2$ to $H_2$ molar ratio of 1:3. However, an experiment reported in J. Catal., 309 (2014) 66-70, which was conducted at the stoichiometric $CO_2$:$H_2$ molar ratio of 1:3, employing the same catalyst "$Cu/ZnO/Al_2O_3$ (I)", the same reaction pressure of 360 bar (equating to a reactant pressure of 331 bar, due to the presence of Ar), and the same temperature and GHSV (260° C. and ca. 10,000 $h^{-1}$ respectively), only achieved a relatively low $CO_2$ conversion (37%) and methanol selectivity (72%) compared to the equivalent reaction performed with a $CO_2$:$H_2$ molar ratio of 1:>10. The reaction performed at a $CO_2$:$H_2$ molar ratio of 1:3 also produced a high level of CO in the product stream, of over 25%.

A key challenge therefore remains, to increase the productivity of methanol by the reaction between $H_2$ and $CO_2$, whilst at the same time avoiding the need to recycle $H_2$ and minimising CO produced by RWGS.

SUMMARY OF THE INVENTION

The invention provides a process for the production of methanol by the stoichiometric hydrogenation of carbon dioxide. The process of the invention can achieve outstanding $CO_2$ conversions (e.g. 90%) and methanol selectivities (>95%), at the stoichiometric reactant ratio of 1:3 ($CO_2$:$H_2$), with good methanol weight time yields of, for instance 1 $g_{MeOH}$ $g_{cat}^{-1}$ $h^{-1}$. Advantageously, the reactant ratio employed means that all or nearly all of the hydrogen can be consumed, which minimises the amount of $H_2$ that needs to be recycled. The outstanding $CO_2$ conversions and methanol selectivites achieved also lead to reduced levels of carbon monoxide product, thereby reducing or avoiding the need to recycle CO. The process can also advantageously be used to synthesise methanol at very high weight time yields (e.g. 4.5 $g_{MeOH}$ $g_{cat}^{-1}$ $h^{-1}$), at high space velocities, again using a stoichiometric molar ratio of $CO_2$ to $H_2$. It is a finding of the invention that such advantages can be achieved under particular high-pressure conditions and above a threshold temperature, using a Cu/ZnO-containing catalyst with a high specific copper surface area. An unexpected effect of the invention is that process is highly productive for methanol; the use of this particular catalyst allows for increasing space velocities while maintaining high conversion and selectivity to methanol. Further advantages are achieved by ensuring that a high proportion of the active sites of the catalyst are present in the accessible diffusion layer of the catalyst, i.e. in the portion of the catalyst that is accessible to the $H_2$ and the $CO_2$ reactants, advantageously giving high weight time yields (e.g. up to 15.3 $g_{MeOH}$ $g_{cat}^{-1}$ $h^{-1}$).

Accordingly, the invention provides a process for producing methanol, which process comprises contacting $H_2$ and $CO_2$ with a solid catalyst, at a temperature of from 200° C. to 300° C. and at a reactant pressure of from 150 bar to 500 bar, which reactant pressure is the sum of the partial pressures of the $H_2$ and the $CO_2$, wherein:

the molar ratio of the $H_2$ to the $CO_2$ is x:1.0, wherein x is from 2.5 to 3.5; and the catalyst comprises (i) a copper component which is Cu, CuO or $Cu_2O$, or a mixture of two or three thereof, and (ii) ZnO. Preferably, the catalyst has a specific copper surface area ($S_{Cu}$) of at least 10 m²/g-catalyst.

DETAILED DESCRIPTION OF THE INVENTION

Figure 1:
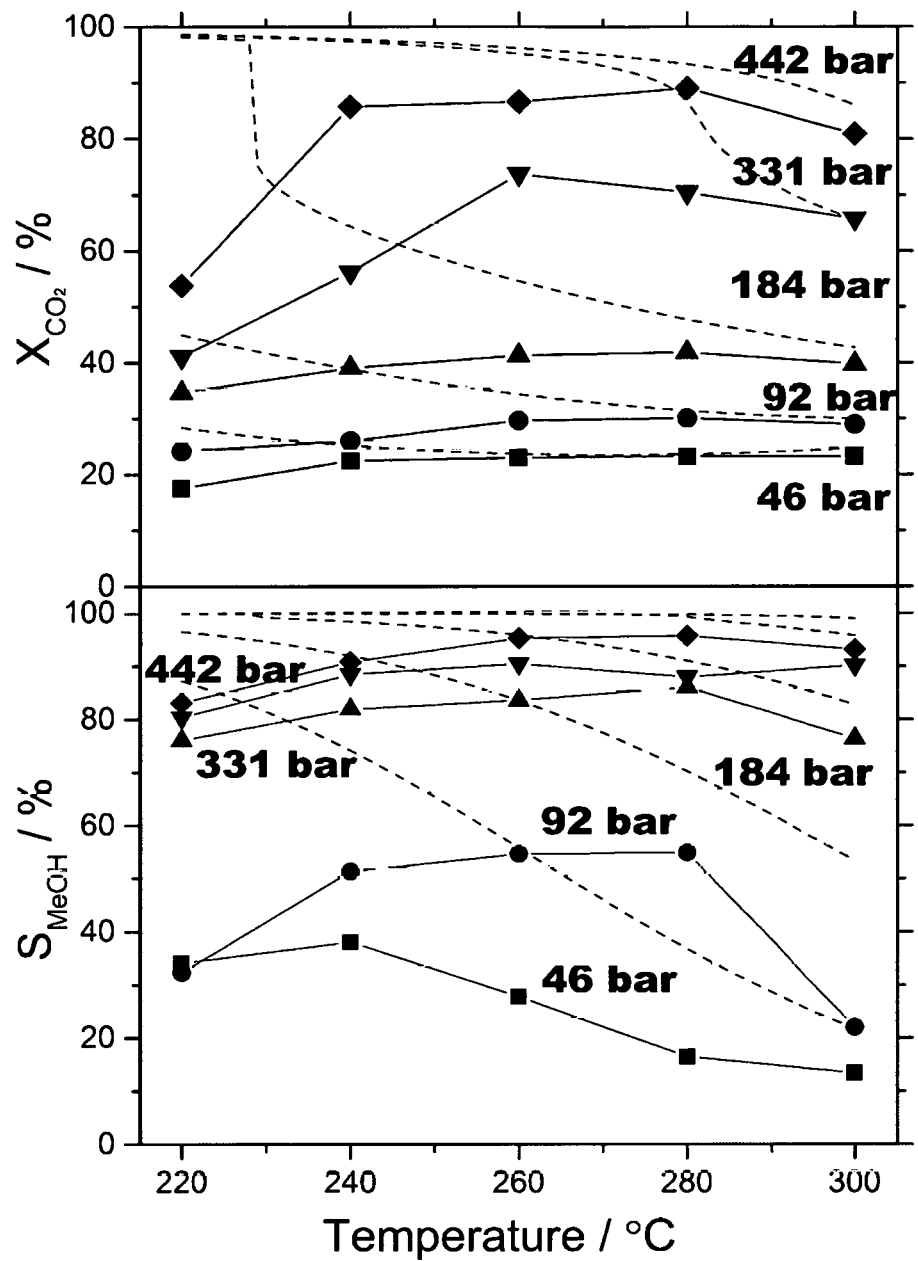
FIG. 1 is a graph showing the effects of reaction temperature and pressure on the $CO_2$ conversion ($X_{CO2}$) and methanol selectivity ($S_{MeOH}$) in the high-pressure stoichiometric hydrogenation of $CO_2$ using a commercial Cu/ZnO/$Al_2O_3$ catalyst at constant GHSV of 10,000 $h^{-1}$ (5.87 NL $g_{cat}^{-1}$ $h^{-1}$). Dotted lines show the theoretical equilibrium $CO_2$ conversion and methanol selectivity. At T=300° C., the dotted lines appear in the same order, from top to bottom, as the solid lines show the experimental results.

The invention relates to a process for producing methanol. The process comprises contacting $H_2$ and $CO_2$ with a solid catalyst, at a temperature of from 200° C. to 300° C. and at a reactant pressure of from 150 bar to 500 bar. The molar ratio of the $H_2$ to the $CO_2$ is x:1.0, wherein x is from 2.5 to 3.5. The catalyst comprises (i) a copper component which is Cu, CuO or $Cu_2O$, or a mixture of two or three thereof, and (ii) ZnO. Preferably, the catalyst has a specific copper surface area ($S_{Cu}$) of at least 10 m²/g-catalyst.

The term "reactant pressure", as used herein, means the sum of the partial pressures of the reactants. In the process of the invention, the reactants are $H_2$ and $CO_2$, and therefore the reactant pressure (of from 150 bar to 500 bar) employed in the present invention refers to the sum of the partial pressures of the $H_2$ and $CO_2$.

The reactants $H_2$ and $CO_2$, and any other components present in addition, may be pre-mixed, i.e. mixed together before the mixture is brought into contact with the catalyst, to form a reactant feed that is then contacted with the catalyst. Alternatively, the reactants can be fed into a reactor separately, in a plurality of different feeds, so that the reactant gases (and any other components present) are mixed together in situ in the presence of the solid catalyst.

As mentioned above, one or more further components may be also present in the reactant feed or feeds that are contacted with the catalyst, in addition to the reactants $H_2$ and $CO_2$. The one or more further components are typically gases. For instance, a non-oxidising gas or an inert gas, may additionally be present. An inert gas component could for example be present as a carrier gas. Nitrogen, or a noble gas, may for instance be present. In some embodiments, a noble gas is present. Often, when a noble gas is present, the noble gas is argon.

The one or more further components present in the reactant feed or feeds may additionally or alternatively include, for example, $H_2O$, which may be present in the form of water vapour or steam. Also, the one or more further components present in the reactant feed or feeds that are brought into contact with the catalyst, may or may not include CO.

In some cases, the reactant feed or feeds do not comprise CO, i.e. CO may be absent from the reactant feed or feeds that are brought into contact with the catalyst.

However, in other embodiments, the reactant feed or feeds do comprise CO. For instance, the process may comprise recycling of unreacted components (i.e. re-feeding) and such unreacted components may include CO. If CO is present in the reactant feed or feeds, it is preferable that the molar ratio of $CO_2$:CO in the feed is high, for instance greater than 10:1, more preferably greater than 100:1, and even more preferably greater than 1000:1, or greater than 10000:1. This is because the invention is concerned with the production of methanol from $CO_2$ and $H_2$, not from CO and $H_2$.

When one or more other gases are present in the reactant feed or feeds, in addition to the $H_2$ and $CO_2$ reactant gases, the total pressure (which may alternatively be referred to as the "reaction pressure") will of course be higher than the sum of the partial pressures of the $H_2$ and the $CO_2$ reactant gases. In other words, the reaction pressure will be higher than the reactant pressure in such cases, the reactant pressure always being the sum of the partial pressures of only the $H_2$ and the $CO_2$.

For instance, if 8 mol % Argon were present in the feed in addition to the $H_2$ and the $CO_2$, and the $H_2$ and the $CO_2$ were present in a 3:1 molar ratio, such that the molar ratio of $CO_2$:$H_2$:Ar were 23:69:8, then if the total pressure (i.e. the "reaction pressure") was, say, 100 bar, the reactant pressure would only be 92 bar. Similarly, a reaction pressure of 50 bar would correspond to a reactant pressure of 46 bar, a reaction pressure of 200 bar would correspond to a reactant pressure of 184 bar, a reaction pressure of 360 bar would correspond to a reactant pressure of 331 bar, and a reaction pressure of 480 bar would correspond to a reactant pressure of 442 bar, if the feed composition consisted of $CO_2$, $H_2$ and Ar in a molar ratio of 23:69:8.

When one or more other components, which would typically be gases, are present in the feed or feeds that are contacted with the catalyst in addition to the $H_2$ and $CO_2$ reactants, the volume ratio of (a) the $H_2$ and $CO_2$ combined, to (b) the other components, (a):(b), may be equal to or greater than 9:1. In other words, the other component or components (usually a gas or gases) may make up equal to or less than 10% by volume of the reactant feed or feeds that are contacted with the catalyst. The other gases may for instance make up equal to or less than 8% by volume of the reactant feed or feeds, or for instance equal to or less than 5% by volume, or equal to or less than 2% by volume. The other gases may for instance make up equal to or less than 1% by volume of the reactant feed or feeds, for instance equal to or less than 0.5% by volume, or equal to or less than 0.1% by volume.

Thus, often, no other gases are present in the reactant feed or feeds that are contacted with the catalyst in addition to the $H_2$ and $CO_2$ reactants. The reactant feed or feeds that are contacted with the catalyst may consist essentially of the $H_2$ and $CO_2$ reactants. The reactant feed or feeds that are contacted with the catalyst may consist of the $H_2$ and $CO_2$ reactants.

Often, for example, the reactant feed or feeds comprise (and more typically consist essentially of, or consist of) the $H_2$ and $CO_2$ reactants, and equal to or less than 10% by volume of an inert gas. More typically the proportion of the inert gas is equal to or less than 8% by volume, for instance equal to or less than 5% by volume, or equal to or less than 2% by volume of an inert gas. The inert gas may for instance make up equal to or less than 1% by volume of the reactant feed or feeds, for instance equal to or less than 0.5% by volume, or equal to or less than 0.1% by volume. The inert gas may be as further defined above, for instance it may be nitrogen or a noble gase. Often, the inert gas is argon.

As discussed above, the molar ratio of the $H_2$ to the $CO_2$ is x:1.0, wherein x is from 2.5 to 3.5. x may for instance be from 2.6 to 3.4, or, say, from 2.7 to 3.3. For example, x may be from 2.8 to 3.2, or, for instance, from 2.9 to 3.1. Preferably, however, x is 3.0.

Alternatively, x may be from 2.5 to 3.3, for instance from 2.6 to 3.2 or, for example, from 2.7 to 3.1. Thus, x may be from 2.8 to 3.1. Again, however, it is preferred that x is from 2.9 to 3.1, for instance about 3.0.

Usually, the step of contacting the $H_2$ and $CO_2$ with the solid catalyst comprises passing the $H_2$ and $CO_2$ over the catalyst.

If another component is present in the reactant feed or feeds, such as one or more further components as further defined above, e.g. argon, then the step of contacting the $H_2$ and $CO_2$ with the solid catalyst typically comprises passing the $H_2$ and $CO_2$, and the one or more other components that are present in the reactant feed or feeds, over the catalyst.

In other words, the process is usually a continuous process (as opposed to a batch process). Usually, passing the $H_2$ and $CO_2$ over the catalyst comprises passing the $H_2$ and $CO_2$ through a reactor comprising said catalyst. Preferably, passing the $H_2$ and $CO_2$ over the catalyst comprises passing the $H_2$ and $CO_2$ through a reactor comprising a fixed bed of the catalyst.

The process of the invention can however be operated as a batch process. Operating the process of the invention as a batch process has the advantage that the contact time between the reactant gases and the catalyst is comparatively very high, leading to very high $CO_2$ conversion and very high methanol selectivity. Thus, the process may be a batch process.

However, a continuous process is preferred. As shown in the Examples herein, when operated as a continuous process, the process of the invention can still afford outstanding $CO_2$ conversions (e.g. 90%) and methanol selectivities (>95%), and at the same time also render good methanol yields of, for instance 1 $g_{MeOH} g_{cat}^{-1} h^{-1}$. Also, at high space velocities, very high methanol yields of, for example, 4.5 $g_{MeOH} g_{cat}^{-1} h^{-1}$, can be achieved, and in some cases even higher yields, for instance 15.3 $g_{MeOH} g_{cat}^{-1} h^{-1}$.

The terms "methanol selectivity" and "selectivity to methanol formation", expressed as a percentage, refer to the molar amount of methanol produced with respect to the total molar amount of all the carbon-containing products obtained by the reaction.

The terms "carbon dioxide conversion" and "$CO_2$ conversion" have the same meaning, and are used interchangeably. They refer to the molar amount of carbon dioxide ($CO_2$) transformed into another chemical compound relative to the initial molar amount of carbon dioxide. In the specific case of a continuous process, they refer to the "carbon dioxide per-pass conversion", i.e. the molar amount of carbon dioxide transformed into another chemical compound relative to the initial molar amount of carbon dioxide, after one pass through the reactor. Alternatively, in the specific case of a batch process, they refer to the molar amount of carbon dioxide transformed into another chemical compound relative to the initial amount of carbon dioxide, at the end of the reaction. In the context of the invention, the conversion is expressed as a percentage and it can be calculated by dividing the number of moles of carbon containing products formed during the process by the number of moles of carbon dioxide initially present.

In the process of the invention, contacting the $H_2$ and $CO_2$ with the solid catalyst typically comprises passing the $H_2$ and $CO_2$ (plus any other component that is present in the reactant feed or feeds, which may be as further defined above, and may, for instance, be argon) over the catalyst at a space velocity of at least 500 $h^{-1}$.

If another component is present in the reactant feed or feeds, such as one or more further components as further defined above, e.g. argon, then the step of contacting the $H_2$ and $CO_2$ with the solid catalyst typically comprises passing the $H_2$ and $CO_2$, and the one or more other components that are present in the reactant feed or feeds, over the catalyst at a space velocity of at least 500 $h^{-1}$.

The term "space velocity", as used herein, refers to the quotient of the entering volumetric flow rate of the reactant feed divided by the volume of the reactor which is occupied by the catalyst (including the catalyst volume), and indicates the reactor volumes of feed that can be treated in a unit time. Space velocity can be expressed as $SV=u_0/V$, where $u_0$ represents the volumetric flow rate of the reactant feed entering the reactor (e.g. expressed in $m^3$ per second or $m^3$ per hour), and V represents the volume of the reactor itself (e.g. expressed in $m^3$) which is occupied by the catalyst (including the catalyst volume). Special values for this measurement exist for liquids and gases, and for systems that use solid catalysts.

The terms "gas hourly space velocity" or "GHSV" have the same meaning and are used interchangeably. GHSV is the specific measurement of the space velocity for gases, and is defined by the volumetric flow rate of the inlet stream at normal pressure (atmospheric pressure) divided by the reactor volume which is occupied by the catalyst (including the catalyst volume).

Typically, the space velocity referred to herein is the gas hourly space velocity.

Thus, typically, in the process of the invention, contacting the $H_2$ and $CO_2$ with the solid catalyst comprises passing the $H_2$ and $CO_2$ over the catalyst at a gas hourly space velocity of at least 500 $h^{-1}$.

If another component is present in the reactant feed or feeds, such as one or more further components as further defined above, e.g. argon, then the step of contacting the $H_2$ and $CO_2$ with the solid catalyst typically comprises passing the $H_2$ and $CO_2$, and the one or more other components that are present in the reactant feed or feeds, over the catalyst at a gas hourly space velocity of at least 500 $h^{-1}$.

The solid catalyst used in the process of the invention comprises zinc oxide (ZnO) and a copper component.

The copper component is Cu, CuO or $Cu_2O$, or a mixture of two or three thereof. Thus, the copper component may be CuO; a mixture of CuO and $Cu_2O$; a mixture of CuO, $Cu_2O$ and Cu; $Cu_2O$; a mixture of CuO and Cu; a mixture of $Cu_2O$ and Cu; or Cu.

The species present in the copper component may depend on the extent to which the copper component has undergone reduction. The copper component can undergo reduction in the presence of hydrogen gas. In particular, some or all of any CuO in the catalyst may be reduced to $Cu_2O$, Cu or a mixture thereof, and some or all of any $Cu_2O$ in the catalyst may be reduced to Cu.

As the skilled person will appreciate, the presence of hydrogen in the reactant feed will typically lead to reduction of this kind.

Also, prior to the step of contacting the $H_2$ and $CO_2$ with the solid catalyst, the process of the invention may further comprise a step of reducing the catalyst. The step of reducing the catalyst may comprise treating the catalyst with hydrogen gas. The treatment with hydrogen gas may be carried out at an elevated temperature, for instance at a temperature above 200° C., and more typically above 300° C. The treatment may be carried out for at least 10 minutes, for instance for at least 30 minutes, or for instance, at least one hour. Such a step will also result in the reduction of some or all of any CuO in the catalyst to $Cu_2O$, Cu or a mixture thereof, and/or the reduction of some or all of any $Cu_2O$ in the catalyst to Cu.

Thus, the copper component in the solid catalyst used in the process of the invention is typically CuO; a mixture of CuO and $Cu_2O$; a mixture of CuO, $Cu_2O$ and Cu; a mixture of $Cu_2O$ and Cu; or Cu. Alternatively, the copper component in the solid catalyst may be $Cu_2O$, or a mixture of CuO and Cu.

Typically, the copper component comprises CuO. Thus, often the copper component is CuO; a mixture of CuO and $Cu_2O$; a mixture of CuO and Cu; or a mixture of CuO, $Cu_2O$ and Cu. It may for instance be CuO; a mixture of CuO and $Cu_2O$; or a mixture of CuO, $Cu_2O$ and Cu.

The copper component of the catalyst also often comprises Cu. Thus, the copper component may be a mixture of CuO, $Cu_2O$ and Cu; a mixture of CuO and Cu; a mixture of $Cu_2O$ and Cu; or Cu. The copper component may for instance be a mixture of CuO, $Cu_2O$ and Cu.

As discussed above, the catalyst employed in the present invention preferably has a specific copper surface area ($S_{Cu}$) of at least 10 $m^2$/g-catalyst.

The term "specific copper surface area" (or "$S_{Cu}$"), as used herein in connection with the catalyst employed in the process of the invention, means the specific copper surface area of the catalyst as determined by nitrous oxide ($N_2O$) pulse chemisorption using the method reported in J. W. Evans, M. S. Wainwright, A. J. Bridgewater, D. J. Young "On the determination of copper surface area by reaction with nitrous oxide", Applied Catalysis, Volume 7, Issue 1, 15 Jul. 1983, pages 75-83.

J. Catal., 309 (2014) 66-70 describes, in the supplementary materials, the determination of the $S_{Cu}$ for catalysts of various compositions using the method disclosed in Evans et al., Applied Catalysis, Vol. 7, 1, 1983, p 75-83, including the determination of the $S_{Cu}$ for the catalyst referred to as "Cu/ZnO/$Al_2O_3$ (I)". According to J. Catal., 309 (2014) 66-70, prior to analysis, samples were reduced in 5% $H_2$ in a He stream at 603 K, followed by cooling to 363 K under He flow. A known volume of $N_2O$ was then injected as pulse by using a six port valve. The $N_2O$ at the exit was trapped in liquid $N_2$ and evolved $N_2$ was measured on the calibrated mass spectrometer, Pffeifer Omnistar GSD 301 C. Copper metal surface areas were calculated assuming $1.46 \times 10^{19}$ copper atoms/$m^2$. The catalyst referred to as "Cu/ZnO/$Al_2O_3$(I)" was found to have an Sc, of only 1.7 $m^2/g_{cat}$ (A. Bansode, A. Urakawa, J. Catal., 309 (2014) 66-70). The catalyst referred to as "Cu/ZnO/$Al_2O_3$(I)" in J. Catal., 309 (2014) 66-70 is the same catalyst that is also employed in many of the reactions described in WO 2013/171239 A1, and is referred to in that document as mixture (IIA).

The catalyst employed in the present invention, on the other hand, generally has a specific copper surface area ($S_{Cu}$), determined by the same method, of at least 10 $m^2/g_{cat}$.

It preferably has an even greater $S_{Cu}$, of, for instance, at least 12 m$^2$/g$_{cat}$. It may for instance have an $S_{Cu}$ of at least 14 m$^2$/g$_{cat}$, for instance an $S_{Cu}$ of at least 15 m$^2$/g$_{cat}$, or at least 16 m$^2$/g$_{cat}$. It may, for example, have an $S_{Cu}$ of at least 17 m$^2$/g$_{cat}$.

The catalyst employed in the present invention may for instance have a specific copper surface area ($S_{Cu}$) of from 10 m$^2$/g$_{cat}$ to 40 m$^2$/g$_{cat}$, or for instance from any of the other lower numerical limits recited in the preceding paragraph, namely from 12 m$^2$/g$_{cat}$, 14 m$^2$/g$_{cat}$, 15 m$^2$/g$_{cat}$, 16 m$^2$/g$_{cat}$ or 17 m$^2$/g$_{cat}$, to 40 m$^2$/g$_{cat}$. The catalyst employed in the present invention may alternatively, for instance, have an $S_{Cu}$ of from 10 m$^2$/g$_{cat}$ to 35 m$^2$/g$_{cat}$, for instance from 12 m$^2$/g$_{cat}$ to 30 m$^2$/g$_{cat}$, or for example from 14 m$^2$/g$_{cat}$ to 25 m$^2$/g$_{cat}$ or, for instance, from 15 m$^2$/g$_{cat}$ to 22 m$^2$/g$_{cat}$, for example from 15 m$^2$/g$_{cat}$ to 20 m$^2$/g$_{cat}$.

Typically, the catalyst employed in the present invention comprises CuO, and has an average CuO crystallite size of equal to or less than 6.0 nm. Often, the catalyst employed in the process of the invention has an average CuO crystallite size of equal to or less than 5.5 nm, or, for instance, equal to or less than 5.0 nm. It usually, for instance, has an average CuO crystallite size of equal to or less than 4.5 nm, for instance, equal to or less than 4.0 nm. Alternatively, the catalyst may have an average CuO crystallite size of greater than 6.0 nm, for instance from 6.0 nm to 8.0 nm. For instance, the catalyst may have an average CuO crystallite size of equal to or less than 8.0 nm.

The average CuO crystallite size of the catalyst may, for instance, be from 1.0 to 6.0 nm, or for instance from 2.0 to 5.5 nm, or from 2.5 to 5.0 nm, for instance from 2.5 to 4.5 nm. It may for instance be from 3.0 to 4.0 nm.

The term "average CuO crystallite size" as used herein, means the average CuO crystallite size as measured by x-ray diffraction (XRD) as described in J. Catal., 309 (2014) 66-70. Thus, an XRD pattern of the catalyst is recorded and the crystallite size of CuO is estimated from the full width at half maximum (FWHM) of corresponding peaks using the Scherrer equation with the shape factor of 0.9 assuming the spherical particles (A. S. Nowick, (1956) X-ray diffraction procedures for polycrystalline and amorphous materials. H. P. Klug and L. E. Alexander. John Wiley and Sons, Inc., New York (1954), *AIChE J.*, 2, 140-140). The (−1 1 1) reflection of CuO is used to determine the average CuO crystallite size.

The amount of the copper component in the catalyst is typically at least 55% by weight. Thus, the catalyst typically comprises equal to or greater than 55% by weight of the copper component. The copper component may be as further defined herein. More typically, the catalyst comprises equal to or greater than 58 weight % of the copper component, for instance equal to or greater than 60 weight % of the copper component. The catalyst may for instance comprise equal to or greater than 61 weight % of the copper component, equal to or greater than 62 weight % of the copper component, or equal to or greater than 63 weight % of the copper component.

The amount of the copper component in the catalyst may for instance be from 55% by weight to 75% by weight. The catalyst may for instance comprise from 58% by weight to 72% by weight of the copper component, or for instance from 60% by weight to 70% by weight, or from 61% by weight to 68% by weight, of the copper component. The catalyst may for example comprise from 62% by weight to 66% by weight of the copper component, for instance from 63% by weight to 65% by weight of the copper component. The copper component may be as further defined anywhere herein.

Alternatively, the catalysts may comprise from 60% by weight to 80% by weight of the copper component. For instance, the catalyst may comprise from 70% by weight to 80% by weight of the copper component.

The catalyst typically comprises equal to or greater than 10% by weight ZnO. More typically, the catalyst comprises equal to or greater than 12 weight % of ZnO, for instance equal to or greater than 15 weight % of ZnO. The catalyst may for instance comprise equal to or greater than 18 weight % of ZnO, equal to or greater than 20 weight % ZnO, or equal to or greater than 22 weight % of ZnO.

The catalyst may for instance comprise from 10% by weight to 35% by weight of ZnO, or for instance from 12% by weight to 32% by weight, or from 15% by weight to 30% by weight, of the ZnO. The catalyst may for example comprise from 18% by weight to 28% by weight of the ZnO, for instance from 20% by weight to 26% by weight of the ZnO, for example from 22% by weight to 25% by weight.

The catalyst may consist of the copper component and the ZnO. In this case, the amount of the copper component in the catalyst may be as defined above, and the balance will be ZnO. Alternatively, the amount of the ZnO may be as defined above, and the balance will be the copper component.

More typically, however, the catalyst further comprises one or more other oxide components. For instance, the catalyst may further comprise one or more oxides selected from oxides of the following elements and from mixed oxides of two or more of the following elements: Al, Mg, Si, Ti, V, Cr, Zr, Mn, La, Ce and Tb.

Thus, the catalyst may further comprise one or more oxides of Al$^{3+}$, Mg$^{2+}$, Si$^{2+}$, Si$^{4+}$, Ti$^{3+}$, Ti$^{4+}$, V$^{2+}$, V$^{3+}$, V$^{4+}$, V$^{5+}$, Cr$^{2+}$, Cr$^{3+}$, Cr$^{6+}$, Zr$^{4+}$, Mn$^{2+}$, Mn$^{3+}$, Mn$^{4+}$, Mn$^{6+}$, La$^{3+}$, Ce$^{3+}$, Ce$^{4+}$ and Th$^{4+}$, including mixed oxides comprising two or more of Mg$^{2+}$, Al$^{3+}$, Si$^{2+}$, Si$^{4+}$, Ti$^{3+}$, Ti$^{4+}$, V$^{2+}$, V$^{3+}$, V$^{4+}$, V$^{5+}$, Cr$^{2+}$, Cr$^{3+}$, Cr$^{6+}$, Zr$^{4+}$, Mn$^{2+}$, Mn$^{3+}$, Mn$^{4+}$, Mn$^{6+}$, La$^{3+}$, Ce$^{3+}$, Ce$^{4+}$ and Th$^{4+}$.

The catalyst may for instance further comprise one, two or more than two different compounds of formula A$_n$X$_m$, wherein A is a cation selected from Al$^{3+}$, Mg$^{2+}$, Si$^{2+}$, Si$^{4+}$, Ti$^{3+}$, Ti$^{4+}$, V+, V$^{3+}$, V$^{4+}$, V+, Cr$^{2+}$, Cr$^{3+}$, Cr$^{6+}$, Zr$^{4+}$, Mn$^{2+}$, Mn$^{3+}$, Mn$^{4+}$, Mn$^{6+}$, La$^{3+}$, Ce$^{3+}$, Ce$^{4+}$ and Th$^{4+}$, X is O$^{2-}$, n is an integer of from 1 to 3, and m is an integer of from 1 to 9, provided that the sum of the positive charges for A$_n$ is equal to the sum of the negative charges for X$_m$.

When the catalyst comprises one or more other such oxide components, the amounts of the copper component and the ZnO in the catalyst are usually as defined above, and typically the balance is made up of the one or more other such oxide components.

Often, the catalyst further comprises Al$_2$O$_3$. When the catalyst comprises Al$_2$O$_3$, it usually comprises at least 2 weight % Al$_2$O$_3$, more typically at least 5 weight % Al$_2$O$_3$, or, for instance, at least 8 weight % Al$_2$O$_3$.

Often, when the catalyst comprises Al$_2$O$_3$, it typically comprises from 2 to 30 weight % Al$_2$O$_3$. It may, for instance comprise from 2 to 25 weight % Al$_2$O$_3$, or for instance from 5 to 25 weight % Al$_2$O$_3$, for example from 5 to 20 weight % Al$_2$O$_3$. The catalyst may for instance comprise from 5 to 15 weight % Al$_2$O$_3$, or for instance from 8 to 12 weight % Al$_2$O$_3$, for example from 9 to 11 weight % Al$_2$O$_3$, e.g. about 10 weight % Al$_2$O$_3$. In one embodiment, the catalyst comprises 10.1 weight % Al$_2$O$_3$.

The catalyst typically further comprises MgO.

Preferably, the catalyst further comprises both Al$_2$O$_3$ and MgO.

When the catalyst comprises MgO, it usually comprises at least 0.2 weight % MgO, more typically at least 0.5 weight % MgO, or, for instance, at least 0.8 weight % MgO. It may for example comprise at least 0.9 weight % MgO, for example at least 1 weight % MgO.

When the catalyst comprises MgO, it typically comprises from 0.2 to 5 weight % MgO. The catalyst may for instance comprise from 0.5 to 3 weight % MgO, for instance from 0.8 to 2 weight % MgO, or for instance from 0.9 to 1.7 weight % MgO. The catalyst may for example comprise from 1 to 2 weight % MgO. In one embodiment, the catalyst comprises 1.3 weight % MgO.

The catalyst often therefore comprises at least 55 weight % of said copper component, at least 10 weight % ZnO, at least 2 weight % $Al_2O_3$, and at least 0.2 weight % MgO. Any of these numerical lower end-points may be as further defined herein.

For instance, the catalyst may comprise at least 55 weight % of said copper component, at least 10 weight % ZnO, at least 5 weight % $Al_2O_3$, and at least 0.5 weight % MgO.

The catalyst may for example comprise at least 55 weight % of said copper component, at least 10 weight % ZnO, from 2 to 30 weight % $Al_2O_3$, and from 0.2 to 5 weight % MgO. Any of these numerical lower or upper end-points may be as further defined herein.

The catalyst may for instance comprise at least 55 weight % of said copper component, at least 15 weight % ZnO, from 5 to 30 weight % $Al_2O_3$, and from 0.5 to 5 weight % MgO.

In one embodiment, the catalyst comprises about 64 weight % CuO, about 25 weight % ZnO, about 10 weight % $Al_2O_3$ and about 1 weight % MgO. The catalyst may for instance comprise 63.5 weight % of said copper component, 24.7 weight % ZnO, 10.1 weight % $Al_2O_3$, and 1.3 weight % MgO.

In another embodiment, the catalyst comprises from 20% by weight to 26% by weight of ZnO and at least 63% by weight of CuO. The catalyst may optionally further comprise from 8% to 12% by weight of $Al_2O_3$ and from 1% to 2% by weight of MgO.

In another embodiment, the catalyst comprises from 20% by weight to 26% by weight of ZnO and at least 74% by weight of CuO. The catalyst comprises about 25% by weight ZnO and about 75% by weight of CuO. For instance, the catalyst may comprise 25.1% by weight of ZnO and 74.9% by weight of CuO. When such catalysts are used, the temperature is typically from 260° C. to 280° C. The catalyst employed in the process of the invention may be a commercially available methanol synthesis catalyst, for instance the Cu/ZnO/$Al_2O_3$ catalyst that is available from Alfa Aesar with product no.: 45776. Alternatively, the catalyst defined herein for use in the process of the invention may be synthesised using a standard co-precipitation method. The co-precipitation method for the preparation of heterogeneous catalysts is well known in the art. It usually comprises the following main steps: precipitation, aging, filtration, washing, drying, and calcination. The precipitation step usually comprises the simultaneous precipitation of the metal salts. During the precipitation, aging, and/or calcination step the basic properties of the catalyst are established. Therefore, catalyst performance can be significantly influenced by changing the precipitation, aging, washing, and/or calcination conditions (Cf. K. P. de jong, "Synthesis of Solid catalyst", Wiley-VCH Verlag GmbH & Co. KGaA., 2009, Weinheim, Chapter. 7. Co-precipitation, pp. 135-151; WO 2013/171239).

The process comprises contacting the $H_2$ and the $CO_2$ with a solid catalyst at a temperature of from 200° C. to 300° C. Often, the temperature is from 210° C. to 295° C., or, for instance, from 220° C. to 295° C. Typically, it is from 225° C. to 290° C., for instance from 230° C. to 290° C. Preferably the temperature is from 250° C. to 300° C., for instance from 250° C. to 290° C., from 255° C. to 285° C., or for example from 260° C. to 280° C. The temperature may, for instance, be from 255° C. to 265° C., for instance about 260° C. In other embodiments, the temperature may be from 275° C. to 285° C., for instance about 280° C.

Contacting the $H_2$ and $CO_2$ with the solid catalyst typically comprises passing the $H_2$ and $CO_2$ (plus any other component that is present in the reactant feed or feeds, which may be as further defined above) over the catalyst at a space velocity of at least 500 $h^{-1}$.

The space velocity is typically however at least 1,000 $h^{-1}$, for instance at least 1,500 $h^{-1}$, or for example at least 2,000 $h^{-1}$.

Often, the space velocity is at least 3,000 $h^{-1}$ or, for instance, at least 3,500 $h^{-1}$. It may for instance be at least 4,000 $h^{-1}$, and may be at least 5,000 $h^{-1}$, or for example at least 6,000 $h^{-1}$ or at least 7,000 $h^{-1}$.

The space velocity may alternatively, for instance, be at least 9,000 $h^{-1}$, for example at least 10,000 $h^{-1}$, or for instance at least 11,000 $h^{-1}$.

Often, however, the space velocity is at least 25,000 $h^{-1}$, more particularly at least 30,000 $h^{-1}$, or for instance at least 35,000 $h^{-1}$.

In some embodiments, the space velocity is at least 40,000 $h^{-1}$, for instance at least 45,000 $h^{-1}$ or for instance at least 50,000 $h^{-1}$.

The space velocity may for instance be at least 55,000 $h^{-1}$, for instance at least 60,000 $h^{-1}$, or for example at least 65,000 $h^{-1}$.

In some embodiments, the space velocity is at least 80,000 $h^{-1}$, for instance at least 90,000 $h^{-1}$ or at least 95,000 $h^{-1}$. The space velocity may, for instance, be at least 100,000 h.

Space velocities of from any of the lower end points disclosed above, up to, say, 150,000 $h^{-1}$ or, for instance, up to 200,000 $h^{-1}$, or even higher, e.g. 250,000 $h^{-1}$, may be employed.

The reactant pressure is often from 160 bar to 500 bar, and may, for instance be from 170 bar to 500 bar, for example from 180 bar to 500 bar. However, in some embodiments, the reactant pressure is from 150 bar to 250 bar, and may, for instance be from 160 bar to 220 bar, for example from 170 bar to 210 bar, or from 180 bar to 200 bar. Preferably, at these pressures, the temperature is from 250° C. to 300° C., more preferably from 250° C. to 290° C., still more preferably from 255° C. to 285° C., or even more preferably from 260° C. to 280° C.

Often, at the temperatures and pressures in the preceding paragraph, a space velocity of at least 10,000 $h^{-1}$ is employed, in which case the process typically comprises producing said methanol at a yield of at least 1.0 $g_{MeOH}$ $g_{cat}^{-1}$ $h^{-1}$. Alternatively, a space velocity of at least 30,000 $h^{-1}$ may be employed at the temperatures and pressures in the preceding paragraph, in which case the process typically comprises producing said methanol at a yield of at least 2.0 $g_{MeOH}$ $g_{cat}^{-1}$ $h^{-1}$. A space velocity of, for instance, at least 50,000 $h^{-1}$ may be employed at the temperatures and pressures in the preceding paragraph, in which case the process typically comprises producing said methanol at a yield of at least 3.0 $g_{MeOH}$ $g_{cat}^{-1}$ $h^{-1}$. Alternatively, a space velocity of at least 90,000 $h^{-1}$ may be employed at the temperatures and pressures in the preceding paragraph, in which case the process typically comprises producing said methanol at a yield of at least 4.0 $g_{MeOH} \, g_{cat}^{-1} \, h^{-1}$. Thus, high methanol yields may be obtained under these conditions.

Alternatively, the reactant pressure may be from 300 bar to 500 bar, or for instance from 310 bar to 500 bar. The reactant pressure may, for instance, be from 320 bar to 500 bar, for example from 325 bar to 500 bar, or from 330 bar to 500 bar. In other embodiments, the reactant pressure is from 300 bar to 400 bar, for instance from 310 bar to 380 bar, or for example from 320 bar to 360 bar, for instance from 325 bar to 350 bar, or from 330 bar to 340 bar. Preferably, at these pressures, the temperature is from 250° C. to 300° C., more preferably from 250° C. to 290° C., still more preferably from 255° C. to 285° C., or even more preferably from 260° C. to 280° C.

Often, at the temperatures and pressures in the preceding paragraph, a space velocity of at least 5,000 $h^{-1}$ is employed, in which case the process typically comprises producing said methanol at a yield of at least 1.0 $g_{MeOH} \, g_{cat}^{-1} \, h^{-1}$. Alternatively, a space velocity of at least 20,000 $h^{-1}$ may be employed at the temperatures and pressures in the preceding paragraph, in which case the process typically comprises producing said methanol at a yield of at least 2.0 $g_{MeOH} \, g_{cat}^{-1} \, h^{-1}$, preferably at a yield of at least 3.0 $g_{MeOH} g_{cat}^{-1} \, h^{-1}$. A space velocity of, for instance, at least 30,000 $h^{-1}$ may be employed at the temperatures and pressures in the preceding paragraph, in which case the process typically comprises producing said methanol at a yield of at least 2.8 $g_{MeOH} \, g_{cat}^{-1} \, h^{-1}$, preferably at a yield of at least 3.0 $g_{MeOH} \, g_{cat}^{-1} \, h^{-1}$. Alternatively, a space velocity of at least 50,000 $h^{-1}$, preferably of at least 60,000 $h^{-1}$, may be employed at the temperatures and pressures in the preceding paragraph, in which case the process typically comprises producing said methanol at a yield of at least 4.0 $g_{MeOH} g_{cat}^{-1} \, h^{-1}$, or a space velocity of at least 90,000 $h^{-1}$ may be employed at the temperatures and pressures in the preceding paragraph, in which case the process typically comprises producing said methanol at a yield of at least 4.5 $g_{MeOH} \, g_{cat}^{-1} \, h^{-1}$.

The reactant pressure may for instance be from 400 bar to 500 bar, or for instance from 410 bar to 500 bar. It may be from 420 bar to 500 bar, for example from 430 bar to 500 bar, or from 440 bar to 500 bar. The reactant pressure may for instance be from 400 bar to 490 bar, for instance from 410 bar to 480 bar, or for example from 430 bar to 480 bar, or for example from 420 bar to 460 bar, for instance from 430 bar to 450 bar, from 435 bar to 450 bar, or from 440 bar to 450 bar. Preferably, at these pressures, the temperature is from 250° C. to 300° C., more preferably from 250° C. to 290° C., still more preferably from 255° C. to 285° C., or even more preferably from 260° C. to 280° C.

Often, at the temperatures and pressures in the preceding paragraph, a space velocity of at least 5,000 $h^{-1}$ is employed, in which case the process typically comprises producing said methanol at a yield of at least 1.0 $g_{MeOH} \, g_{cat}^{-1} \, h^{-1}$. Alternatively, a space velocity of at least 9,000 $h^{-1}$ may be employed at the temperatures and pressures in the preceding paragraph, in which case the process typically comprises producing said methanol at a yield of at least 2.0 $g_{MeOH} \, g_{cat}^{-1} \, h^{-1}$, preferably at a yield of at least 3.0 $g_{MeOH} \, g_{cat}^{-1} \, h^{-1}$. A space velocity of, for instance, at least 20,000 $h^{-1}$ may be employed at the temperatures and pressures in the preceding paragraph, in which case the process typically comprises producing said methanol at a yield of at least 3.0 $g_{MeOH} \, g_{cat}^{-1} \, h^{-1}$. Alternatively, a space velocity of at least 30,000 $h^{-1}$ or at least 40,000 $h^{-1}$ may be employed at the temperatures and pressures in the preceding paragraph, in which case the process typically comprises producing said methanol at a yield of at least 4.0 $g_{MeOH} \, g_{cat}^{-1} \, h^{-1}$, or for instance at a yield of at least 6.0 $g_{MeOH} \, g_{cat}^{-1} \, h^{-1}$. A space velocity of at least 70,000 $h^{-1}$ may be employed at the temperatures and pressures in the preceding paragraph, in which case the process typically comprises producing said methanol at a yield of at least 4.5 $g_{MeOH} \, g_{cat}^{-1} \, h^{-1}$, or for instance at a yield of at least 10.0 $g_{MeOH} \, g_{cat}^{-1} \, h^{-1}$.

Often, the process comprises producing said methanol at a yield of at least 1.0 $g_{MeOH} \, g_{cat}^{-1} \, h^{-1}$. The process may for instance comprise producing said methanol at a yield of at least 2.0 $g_{MeOH} \, g_{cat}^{-1} \, h^{-1}$, or, for instance at a yield of at least 3.0 $g_{MeOH} \, g_{cat}^{-1} \, h^{-1}$. Preferably, the process comprises producing said methanol at a yield of at least 3.5 $g_{MeOH} \, g_{cat}^{-1} \, h^{-1}$, for instance at a yield of at least 4.0 $g_{MeOH} \, g_{cat}^{-1} \, h^{-1}$, or at a yield of at least 4.5 $g_{MeOH} \, g_{cat}^{-1} \, h^{-1}$. In certain embodiments, the process comprises producing said methanol at a yield of at least 6.0 $g_{MeOH} \, g_{cat}^{-1} \, h^{-1}$, for instance at a yield of at least 10.0 $g_{MeOH} \, g_{cat}^{-1} \, h^{-1}$, or at a yield of at least 15.0 $g_{MeOH} \, g_{cat}^{-1} \, h^{-1}$.

In the process of the invention, the selectivity of the process for methanol formation is typically at least 60%, and more typically at least 70%. The selectivity of the process for methanol formation may for instance be at least 80%, and is often at least 90%, for instance at least 93%, or for instance at least 95%.

In the process of the invention, the $CO_2$ conversion, which is typically the conversion of $CO_2$ per pass, is at least 40%. Preferably, it is at least 60%, and more preferably it is at least 70%, or for instance at least 75%, for example at least 80%.

In one embodiment of the invention, the selectivity of the process for methanol formation is at least 80%, the space velocity is from 500 $h^{-1}$ to 50,000 $h^{-1}$, and, preferably, the reactant pressure is from 320 bar to 500 bar.

The selectivity of the process for methanol formation may for instance be at least 90%, and the space velocity may be from 500 $h^{-1}$ to 20,000 $h^{-1}$, preferably from 1,000 $h^{-1}$ to 20,000 $h^{-1}$. Typically, in this embodiment, the reactant pressure is from 320 bar to 450 bar.

Alternatively, the selectivity of the process for methanol formation may for instance be at least 90%, the space velocity may be from 500 $h^{-1}$ to 3,000 $h^{-1}$. Preferably, the reactant pressure is from 150 bar to 300 bar, for instance from 160 bar to 250 bar, or from 170 bar to 200 bar.

In the process of the invention, the conversion of $CO_2$ per pass may be at least 40%, and the space velocity may be from 500 $h^{-1}$ to 60,000 $h^{-1}$, for instance from 500 $h^{-1}$ to 50,000 $h^{-1}$, or for example from 500 $h^{-1}$ to 20,000 $h^{-1}$. The reactant pressure may be from 200 to 500 bar but is preferably from 320 to 500 bar.

The conversion of $CO_2$ per pass may for instance be at least 40%, the space velocity may be from 500 $h^{-1}$ to 70,000 $h^{-1}$, and the reactant pressure may be from 420 to 500 bar.

The conversion of $CO_2$ per pass may for instance be at least 75%, for instance at least 80%, the space velocity may be from 500 $h^{-1}$ to 30,000 $h^{-1}$, preferably from 500 $h^{-1}$ to 20,000 $h^{-1}$ and the reactant pressure may be from 420 to 450 bar. Alternatively, the space velocity may be from 500 $h^{-1}$ to 5,000 $h^{-1}$, and the reactant pressure may be from 320 to 500 bar, for instance from 320 to 450 bar.

Often, in the process of the invention, the reactant pressure is from 320 to 500 bar, and preferably from 320 to 450 bar, the space velocity is from 500 $h^{-1}$ to 30,000 $h^{-1}$, the selectivity of the process for methanol formation is at least 80%, and the conversion of $CO_2$ per pass is at least 40%, and preferably at least 60%.

Typically, the reactant pressure is from 320 to 500 bar, and preferably from 320 to 450 bar, the space velocity is from 500 h$^{-1}$ to 15,000 h$^{-1}$, the selectivity of the process for methanol formation is at least 90%, and the conversion of $CO_2$ per pass is at least 60%.

The reactant pressure may for instance be from 420 to 500 bar, and is preferably from 420 to 450 bar, the space velocity may be from 500 h$^{-1}$ to 15,000 h$^{-1}$, the selectivity of the process for methanol formation may be at least 90%, and the conversion of $CO_2$ per pass may be at least 80%.

In some embodiments of the invention, the reactant pressure is from 320 to 500 bar, and preferably from 320 to 450 bar, the space velocity is at least 5,000 h$^{-1}$ and the process comprises producing said methanol at a yield of at least 1.0 $g_{MeOH} g_{cat}^{-1} h^{-1}$. Alternatively, the reactant pressure may be from 320 to 500 bar, and is preferably from 320 to 450 bar, the space velocity may be at least 10,000 h$^{-1}$, preferably at least 20,000 h$^{-1}$, and the process comprises producing said methanol at a yield of at least 2.0 $g_{MeOH} g_{cat}^{-1} h^{-1}$.

The reactant pressure may for instance be from 320 to 500 bar, and is preferably from 320 to 450 bar, the space velocity may be at least 20,000 h$^{-1}$, preferably at least 50,000 h$^{-1}$, more preferably at least 60,000 h$^{-1}$, and the process may comprise producing said methanol at a yield of at least 4.0 $g_{MeOH} g_{cat}^{-1} h^{-1}$.

The reactant pressure may for instance be from 320 to 500 bar, and is preferably from 320 to 450 bar, the space velocity may be at least 30,000 h$^{-1}$, preferably at least 90,000 h$^{-1}$, more preferably at least 100,000 h$^{-1}$, and the process may comprise producing said methanol at a yield of at least 5.0 $g_{MeOH} g_{cat}^{-1} h^{-1}$.

In some embodiments of the invention, the reactant pressure is from 320 bar to 500 bar and the space velocity is from 5,000 h- to 110,000 h$^{-1}$, preferably from from 5,000 h$^{-1}$ to 30,000 h$^{-1}$. In addition, preferably the selectivity of the process for methanol formation is at least 80%, the conversion of $CO_2$ per pass is at least 40%, and the process comprises producing said methanol at a yield of at least 1.0 $g_{MeOH} g_{cat}^{-1} h^{-1}$.

In some embodiments of the invention, the reactant pressure is from 320 bar to 500 bar and the space velocity is from 5,000 h$^{-1}$ to 110,000 h$^{-1}$, preferably from from 5,000 h$^{-1}$ to 40,000 h$^{-1}$, more preferably from 20,000 h$^{-1}$ to 40,000 h$^{-1}$. In addition, preferably the selectivity of the process for methanol formation is at least 85%, the conversion of $CO_2$ per pass is at least 45%, and the process comprises producing said methanol at a yield of at least 1.5 $g_{MeOH} g_{cat}^{-1} h^{-1}$.

In some embodiments of the invention, the reactant pressure is from 320 bar to 500 bar and the space velocity is from 5,000 h$^{-1}$ to 110,000 h$^{-1}$, preferably from from 5,000 h$^{-1}$ to 40,000 h$^{-1}$, more preferably from from 20,000 h$^{-1}$ to 40,000 h$^{-1}$. In addition, preferably the selectivity of the process for methanol formation is at least 95%, the conversion of $CO_2$ per pass is at least 75%, and the process comprises producing said methanol at a yield of at least 2.0 $g_{MeOH} g_{cat}^{-1} h^{-1}$.

In other embodiments of the invention, the reactant pressure is from 150 to 250 bar, and the space velocity is at least 50,000 h$^{-1}$ and, preferably, the process comprises producing said methanol at a yield of at least 3.0 $g_{MeOH} g_{cat}^{-1} h^{-1}$.

In other embodiments of the invention, the reactant pressure is from 150 to 250 bar, and the space velocity is at least 30,000 h$^{-1}$ and, preferably, the process comprises producing said methanol at a yield of at least 2.0 $g_{MeOH} g_{cat}^{-1} h^{-1}$.

The present inventors have found that remarkable further improvements can be achieved by ensuring that a high proportion of the active sites of the catalyst are present in a portion of the catalyst that is accessible to the $H_2$ and the $CO_2$ reactants. The portion of the catalyst that is accessible to the reactants is known as the "accessible diffusion layer" of the catalyst.

The inventors have found that, under the conditions of the process of the invention, and especially at the higher pressures when gases tend to liquefy, the reactants need to diffuse between the catalyst particles to access the catalyst active sites. When the accessible diffusion layer of the catalyst is not large enough, part of the catalyst is not taking part in the process and this can result in lower yields (as expressed in grams of methanol produced per gram of catalyst per hour). The inventors have found that this situation can be improved by increasing the proportion of the active sites of the catalyst that belong to the accessible diffusion layer. There are several ways in which this may be achieved, including, but not limited to, lowering the size of the catalyst particle, engineering the catalyst, or supporting the catalyst on a catalyst support, such as on a membrane or other type of support.

The proportion of the active sites of the catalyst that belong to the accessible diffusion layer may be expressed as a percentage, and it is preferred that, for instance, at least 70% of the active sites of the catalyst belong to the accessible diffusion layer.

Accordingly, in the process of the invention, it is preferred that the portion of the catalyst that is accessible to said $H_2$ and said $CO_2$ comprises at least 70% of the active sites of the catalyst. More preferably, the portion of the catalyst that is accessible to said $H_2$ and said $CO_2$ comprises at least 80% of the active sites of the catalyst. Even more preferably, the portion of the catalyst that is accessible to said $H_2$ and said $CO_2$ comprises at least 90% of the active sites of the catalyst, for instance at least 95% of the active sites of the catalyst, at least 98% of the active sites of the catalyst, or for example at least 99% of the active sites of the catalyst. Most preferably, the portion of the catalyst that is accessible to said $H_2$ and said $CO_2$ comprises all, or substantially all (e.g. greater then 99.5%, or greater than 99.9%), of the active sites of the catalyst.

As mentioned above, one way to increase the proportion of the active sites of the catalyst that belong to the accessible diffusion layer is to reduce the catalyst's particle size.

The term "particle size" as used herein means the diameter of the particle if the particle is spherical or, if the particle is non-spherical, the volume-based particle size. The volume-based particle size is the diameter of the sphere that has the same volume as the non-spherical particle in question.

The catalyst employed in the present invention often has a particle size of from about 80 μm to about 320 μm, for instance from about 100 μm to about 300 μm.

However, the present inventors have found that remarkable further improvements can be achieved when the catalyst has an even smaller particle size than this, in order to increase the proportion of the active sites of the catalyst that belong to the accessible diffusion layer. Such further improvements have been observed for instance when a catalyst particle size of less than 80 μm is employed, and in particular when a particle size of equal to or less than 50 μm is employed, for instance a particle size of equal to or less than 30 μm, or for example a particle size of equal to or less than 20 μm.

Accordingly, preferably the catalyst employed in the process of the invention has a particle size of equal to or less than 50 μm, for instance, a particle size of equal to or less than 30 μm, such as, for example a particle size of less than or equal to 20 μm.

The particle size of the catalyst in these embodiments may for instance be from 5 μm to 80 μm, or for instance from 5 μm to 50 μm, such as, for example, from 10 μm to 30 μm, or for instance from 10 μm to 25 μm.

The following further preferences and embodiments are particularly applicable to the use of catalysts in which a high proportion of the active sites of the catalyst are present in the portion of the catalyst that is accessible to the $H_2$ and the $CO_2$ reactants (i.e. in the "accessible diffusion layer"). The following preferences and embodiments are therefore particularly applicable to the use of catalysts which have small catalyst particle sizes, in the present invention, e.g. catalysts with a particle size of less than 80 μm. When catalysts are employed in which a high proportion of the active sites of the catalyst are present in the accessible diffusion layer, e.g. when such a small particle size is employed, this results in remarkable further improvements in methanol selectivity, $CO_2$ conversion, and methanol yield.

For instance, in some embodiments, the selectivity of the process for methanol formation is at least 80%, preferably at least 90%, the space velocity is from 500 $h^{-1}$ to 110,000 $h^{-1}$, and preferably from 500 $h^{-1}$ to 70,000 $h^{-1}$; and the reactant pressure is preferably from 320 bar to 500 bar, more preferably from 320 bar to 450 bar, or from 420 to 500 bar, for instance from 420 to 450 bar.

In other embodiments, the conversion of $CO_2$ per pass is at least 40%, preferably at least 75%; the space velocity is from 500 $h^{-1}$ to 110,000 $h^{-1}$, preferably from 500 $h^{-1}$ to 40,000 $h^{-1}$; and the reactant pressure is from 320 to 500 bar, preferably from 420 to 500 bar, more preferably from 420 to 450 bar.

In some embodiments, the reactant pressure is from 320 to 500 bar, preferably from 320 to 450 bar, the space velocity is from 500 $h^{-1}$ to 110,000 $h^{-1}$, preferably from 500 $h^{-1}$ to 40,000 $h^{-1}$, the selectivity of the process for methanol formation is at least 80%, and the conversion of $CO_2$ per pass is at least 40%.

For instance, the reactant pressure may be from 320 to 500 bar, preferably from 320 to 450 bar, the space velocity may be from 500 $h^{-1}$ to 15,000 $h^{-1}$, the selectivity of the process for methanol formation may be at least 90%, and the conversion of $CO_2$ per pass may be at least 60%.

The reactant pressure may for instance be from 420 to 500 bar, preferably from 420 to 450 bar, the space velocity may be from 500 $h^{-1}$ to 40,000 $h^{-1}$, preferably from 500 $h^{-1}$ to 15,000 $h^{-1}$, the selectivity of the process for methanol formation is at least 90%, and the conversion of $CO_2$ per pass is at least 80%.

In some embodiments, the reactant pressure is from 320 to 500 bar, preferably from 320 to 450 bar, the space velocity is at least 5,000 $h^{-1}$ and the process comprises producing said methanol at a yield of at least 1.5 $g_{MeOH} g_{cat}^{-1} h^{-1}$, more preferably at a yield of at least 2.0 $g_{MeOH} g_{cat}^{-1} h^{-1}$.

For instance the reactant pressure may be from 320 to 500 bar, preferably from 320 to 450 bar, the space velocity may be at least 20,000 $h^{-1}$ and the process may comprise producing said methanol at a yield of at least 3.0 $g_{MeOH} g_{cat}^{-1} h^{-1}$, more preferably at a yield of at least 6.0 $g_{MeOH} g_{cat}^{-1} h^{-1}$.

The reactant pressure may for example be from 320 to 500 bar, preferably from 320 to 450 bar, the space velocity may be at least 50,000 $h^{-1}$, preferably at least 60,000 $h^{-1}$, and the process may comprise producing said methanol at a yield of at least 4.0 $g_{MeOH} g_{cat}^{-1} h^{-1}$, and preferably at a yield of at least 10.0 $g_{MeOH} g_{cat}^{-1} h^{-1}$.

In some embodiments, the reactant pressure is from 320 to 500 bar, preferably from 320 to 450 bar, the space velocity is at least 90,000 $h^{-1}$, preferably at least 100,000 $h^{-1}$, and the process comprises producing said methanol at a yield of at least 5.0 $g_{MeOH} g_{cat}^{-1} h^{-1}$, and preferably at a yield of at least 15.0 $g_{MeOH} g_{cat}^{-1} h^{-1}$.

In other preferred embodiments of the invention, the reactant pressure is from 320 bar to 500 bar; and the space velocity is from 5,000 $h^{-1}$ to 40,000 $h^{-1}$, preferably from 20,000 $h^{-1}$ to 40,000 $h^{-1}$; and preferably: the selectivity of the process for methanol formation is at least 85%, the conversion of $CO_2$ per pass is at least 45%, and the process comprises producing said methanol at a yield of at least 1.5 $g_{MeOH} g_{cat}^{-1} h^{-1}$, and preferably at a yield of at least 3.0 $g_{MeOH} g_{cat}^{-1} h^{-1}$; or For instance, in some embodiments, the reactant pressure is from 420 bar to 500 bar; and the space velocity is from 5,000 $h^{-1}$ to 40,000 $h^{-1}$, preferably from 20,000 $h^{-1}$ to 40,000 $h^{-1}$; and preferably: the selectivity of the process for methanol formation is at least 95%, the conversion of $CO_2$ per pass is at least 75%, and the process comprises producing said methanol at a yield of at least 2.0 $g_{MeOH} g_{cat}^{-1} h^{-1}$, and preferably at a yield of at least 6.0 $g_{MeOH} g_{cat}^{-1} h^{-1}$.

The present invention is further illustrated in the Examples which follow.

EXAMPLES

Example 1

Experimental Procedure

A continuous flow, high-pressure fixed-bed reactor was used to study the hydrogenation of $CO_2$ to methanol. The reactor made of stainless steel was in a tubular shape with outer diameter of ⅛" or ¼" with inner diameter of 0.07" or 0.12", respectively. The details of high-pressure fixed-bed reactor and analytical systems are described in A. Bansode, B. Tidona, P. R. von Rohr, A. Urakawa, Catal. Sci. Technol., 3 (2013) 767-778. The reactant gas mixture (molar ratio of $CO_2:H_2:Ar=23:69:8$) was purchased from Abelló Linde (Spain). A commercial methanol synthesis catalyst (Cu/ZnO/Al$_2$O$_3$, Product No.: 45776) was purchased from Alfa Aesar. The catalyst pellet was crushed, sieved to particle size of 100-300 μm, and charged to the reactor with approximate catalytic bed length of 20-100 mm depending on the amount of catalyst defined by the desired reaction conditions. Prior to the reaction, the catalyst was reduced in hydrogen stream (molar ratio of $H_2:Ar=90:10$) at 20 ml min$^{-1}$ for 2 h at 330° C. at atmospheric pressure. Subsequently, the catalyst bed was cooled down to room temperature and pressurized using pre-mixed reactant gas to a desired reaction pressure. A high-pressure syringe pump (Teledyne ISCO 260D) was used to dispense the premixed reactant gases to precisely control the $CO_2$ to $H_2$ molar ratio. For GHSV of 650 $h^{-1}$, the ¼" reactor tube with 1.0 g of the catalyst was used, while for higher GHSV conditions (2,000-8,000 $h^{-1}$ and 10,000-100,000 $h^{-1}$) the ⅛" reactor tube with 400 and 50 mg of the catalyst was used.

Table 1 below shows (i) the composition of the as-purchased commercial methanol synthesis catalyst (Cu/ZnO/Al$_2$O$_3$, Alfa Aesa Product No.: 45776), (ii) the copper surface area ($S_{Cu}$) of the catalyst after reduction pretreatment, and (iii) the average crystallite size of the CuO in the catalyst. The Cu surface area ($S_{Cu}$) was determined by $N_2O$ pulse chemisorption (A. Bansode, A. Urakawa, J. Catal., 309 (2014) 66-70) using the method previously reported in J. W. Evans et al., Applied Catalysis, Vol. 7, 1, 1983, p 75-83.

TABLE 1

Elemental composition, Cu surface area and average crystallite size of the commercial catalyst used

| Catalyst | Elemental analysis (wt %) | | | | $S_{Cu}$ ($m^2/g_{cat}$) | Cryst. size of CuO (nm) |
|---|---|---|---|---|---|---|
| | CuO | ZnO | $Al_2O_3$ | MgO | | |
| Alfa Aesa Product No. 45776 | 63.5 | 24.7 | 10.1 | 1.3 | 17.5 | 3.9 |

Continuous $CO_2$ hydrogenation to methanol was tested at five different pressure conditions of 50, 100, 200, 360 and 480 bar. However, considering that 8 mol % Ar was also present in the feed composition, the reactant pressure, i.e. the sum of the partial pressures of $CO_2$ and $H_2$, was 46, 92, 184, 331 and 442 bar, respectively.

GHSV is defined by the volumetric flow rate of inlet stream at normal pressure divided by the reactor volume where the catalyst is packed (including the catalyst volume). A wide range of GHSV conditions (650-100,000 $h^{-1}$) were examined. GHSV is also shown in catalyst-mass-normalized unit, in which the value ranges from 0.37 to 49.85 NL $g_{cat}^{-1}$ $h^{-1}$.

For the GHSV calculation in both units, the total flow rate at normal pressure including Ar was used. The vaporized outlet stream were injected to GC every ca. 12 min for 3 h at each condition of temperature, pressure and GHSV and an averaged value was taken. No catalyst deactivation was detected for the duration of catalytic tests performed.

Thermodynamic Calculations

Figure 4:
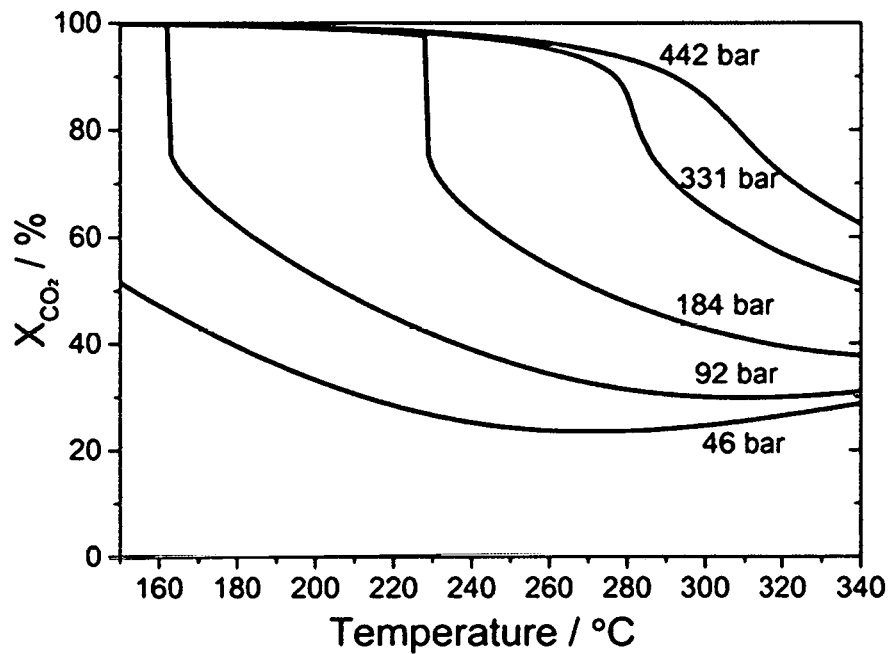
FIG. 4 is a graph showing the theoretical equilibrium conversion of $CO_2$ ($X_{CO2}$) under different pressure conditions as a function of temperature at $CO_2$:$H_2$=1:3.
Figure 5:
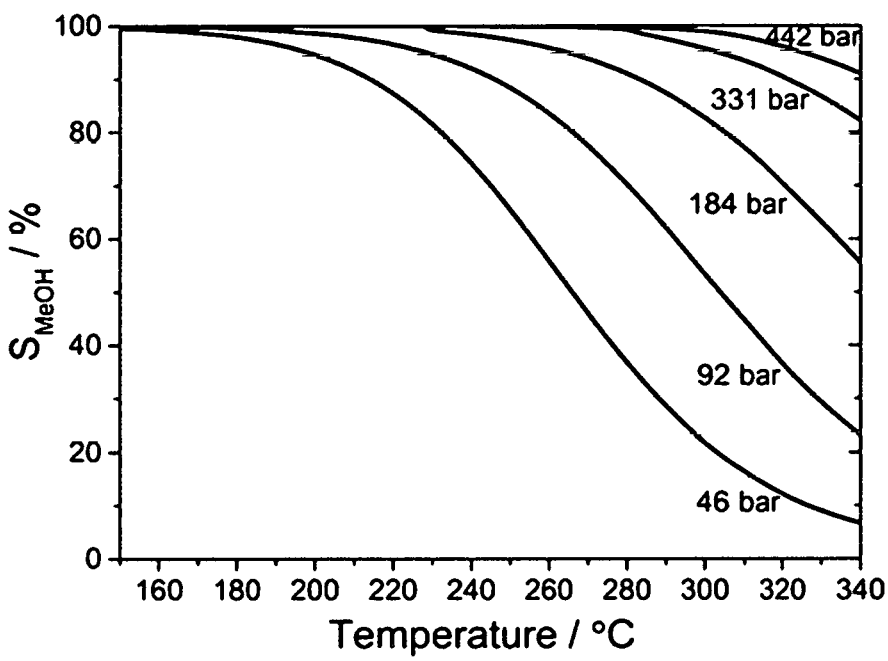
FIG. 5 is a graph showing the theoretical methanol selectivity ($S_{MeOH}$) at equilibrium under different pressure conditions as a function of temperature using $CO_2$:$H_2$ ratio=1:3.

The thermodynamic calculations were performed using Aspen HYSYS V8.6 simulation tool using the Soave Redlich Kwong (SRK) equation of state (EOS) with modified binary interaction parameters for CO, $CO_2$, $H_2$, methanol and water being taken from the optimized values reported by van Bennekom et al. for methanol synthesis (J. G. van Bennekom, J. G. M. Winkelman, R. H. Venderbosch, S. D. G. B. Nieland, H. J. Heeres, Ind. Eng. Chem. Res., 51 (2012) 12233-12243). The calculations were performed by minimization of Gibbs free energy. Methane was not considered in all calculations. FIG. 4 depicts the equilibrium conversion of $CO_2$ and FIG. 5 depicts the equilibrium selectivity of methanol at 46, 92, 184, 331, 442 bar and temperature range of 150 to 340° C.

Results and Discussion

Effects of Temperature Under High-Pressure Conditions

First, the effects of temperature on $CO_2$ conversion and methanol selectivity were examined at the reactant pressures of 46, 92, 184, 331, and 442 bar (FIG. 1). The catalytic tests were performed at a constant GHSV of 10,000 $h^{-1}$, although, as discussed in the next section, this reaction parameter can directly influence the residence time of the reactants in the reactor and thus catalytic performance. $CO_2$ conversion and methanol selectivity are presented in comparison with the theoretical equilibrium values.

The advantages of high-pressure conditions can be seen from the thermodynamic calculations (FIG. 1, dotted lines). At 46 bar, $CO_2$ conversion varies between 25-30% with rapidly decreasing methanol selectivity from ca. 90 to 20% in the temperature window of 220-300° C. At 92 bar, $CO_2$ conversion varies from roughly 50% (220° C.) to 30% (300° C.) with very good to moderate methanol selectivity (96.5% at 220° C. and 53.4% at 300° C.), whereas at the highest examined pressure of 442 bar, theoretically $CO_2$ can be effectively converted to methanol (98.7% at 220° C. and 86.1% at 300° C.) with very high selectivity for the entire temperature range (>99.9% at 220° C. and 99.0% at 300° C.). At the intermediate pressures examined (184 and 331 bar), there was a sudden change in $CO_2$ equilibrium conversion at ca. 230 and 280° C., respectively (this change also takes place at 92 bar but at much lower temperature (ca. 160° C.), FIG. 4). This is due to enhanced $CO_2$ conversion induced by the phase transition and separation (formation of liquid phase) associated with the condensation of the products when the reaction temperature is lower than the transition point. Such phase separation allows $CO_2$ conversion to methanol beyond one-phase equilibrium, as precisely described and demonstrated by Heeres and coworkers (J. G. van Bennekom, R. H. Venderbosch, J. G. M. Winkelman, E. Wilbers, D. Assink, K. P. J. Lemmens, H. J. Heeres, Chem. Eng. Sci., 87 (2013) 204-208). The positive impact of such phase separation on $CO_2$ conversion becomes less prominent at higher pressures as noticeable from the equilibrium $CO_2$ conversion curves of 184 and 331 bar. At 442 bar the impact becomes unnoticeable. This tendency is attributed to the highly dense reactant/product mixture whose density only differs slightly from that of the liquid products and/or it indicates that they are simply miscible at the high-pressure condition.

Experimentally, the general advantages of high-pressure conditions in $CO_2$ conversion, methanol selectivity, and thus methanol yield were confirmed with better catalytic performance at higher pressures (FIG. 1). Besides methanol, CO was found as the only major product arising from RWGS reaction. Another product observed was methane with a minor quantity (<0.8%). In comparison to the theoretical equilibrium, larger deviations were observed at lower temperatures for both $CO_2$ conversion and methanol selectivity. These two key indicators of reaction performance showed the maxima at 260-280° C., except methanol selectivity at 331 bar, and then decreased at higher temperatures. The slight performance deterioration above the optimum temperature of 260-280° C. is in accordance with the trend expected by the theoretical equilibrium. In the range of 220-300° C. there were smaller deviations between experimental and theoretical $CO_2$ conversion and methanol selectivity above the optimum temperature, whereas larger deviations were found below the optimum temperature. This implies that thermodynamic equilibrium has been reached or, at least, has significant effects at the temperatures higher than the optimum temperature at each pressure condition. In other words, at the temperatures below the maxima in catalytic performance, the reaction is kinetically controlled due to poor reaction rates determined by the catalyst at the low temperatures. Theoretically, $CO_2$ conversion can be drastically boosted below 230° C. at 184 bar. However, such performance enhancement was not observed and a very poor value was obtained at 220° C. This is a clear indication that the reaction is kinetically controlled at the temperature. To fully benefit from the phase separation, the reaction has to be performed at lower GHSV to achieve high reaction rates at low temperatures. Also, it is important to remark that the advantageous phase separation is expected to take place theoretically at higher temperatures under higher pressure conditions. Therefore, high-pressure conditions can be greatly beneficial in this respect to achieve phase separation under kinetically favorable high-temperature conditions.

The best catalytic performance in terms of $CO_2$ conversion and methanol selectivity was obtained at 260° C. at 331 bar and at 280° C. at 46, 92, 184, and 442 bar. Maximally performing reaction temperatures were examined at higher and lower GHSV conditions at 331 bar. Interestingly, it was found that the optimum temperature remained the same irrespective of different GHSV conditions (data are not shown). Therefore, the optimum temperatures were taken at the respective pressures for the study described below where the influence of GHSV on catalytic performance was investigated.

Effects of GHSV Under High-Pressure Conditions

Figure 2:
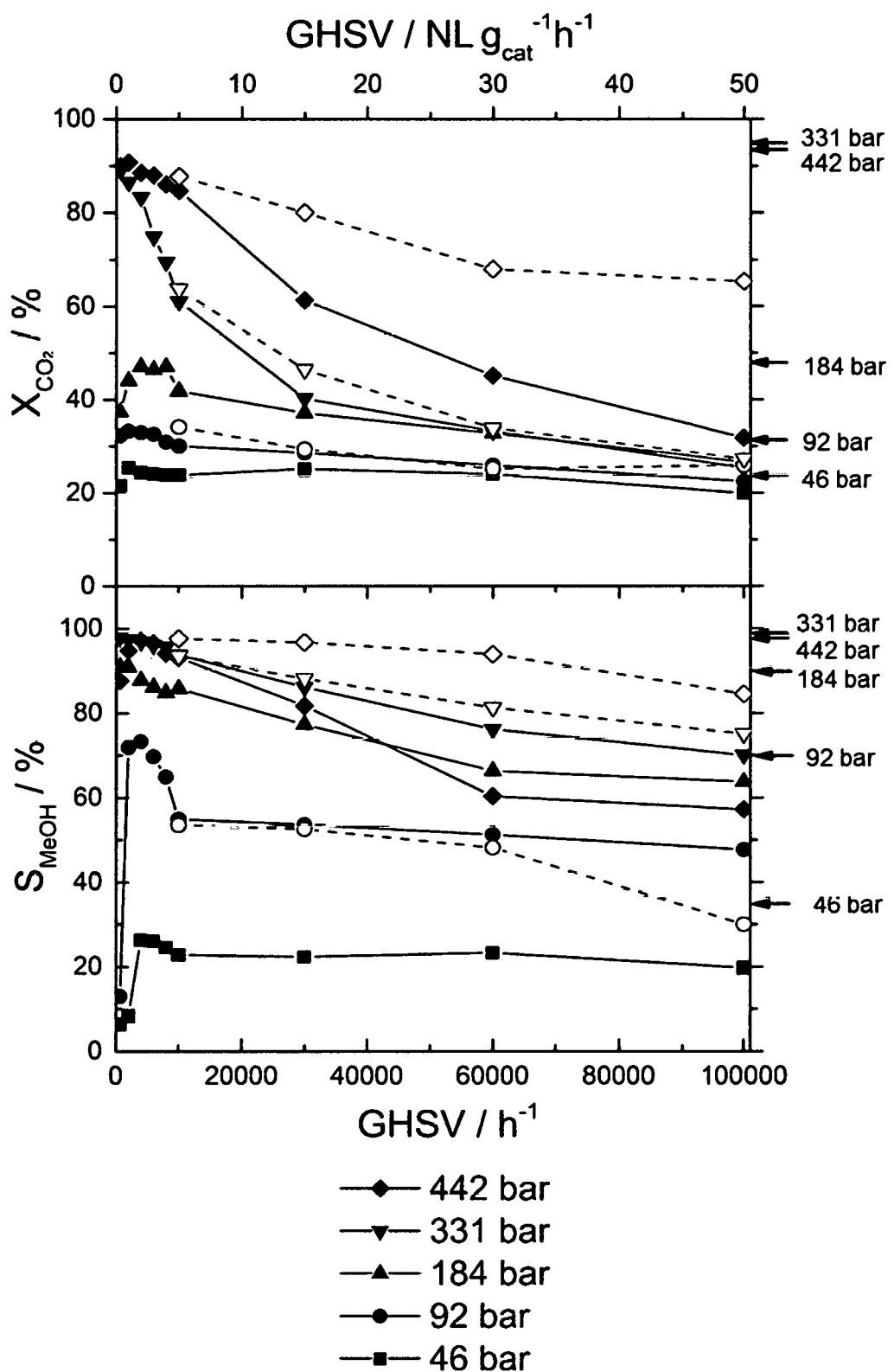
FIG. 2 is a graph showing the $CO_2$ conversion ($X_{CO2}$) and methanol selectivity ($S_{MeOH}$) in the high-pressure stoichiometric $CO_2$ hydrogenation under different GHSV conditions (650-100,000 $h^{-1}$, equivalent to 0.37-49.85 NL $g_{cat}^{-1}$ $h^{-1}$) at 280° C. (46, 92, 184, and 442 bar) and at 260° C. (331 bar) using a commercial Cu/ZnO/$Al_2O_3$ catalyst. The filled symbols correspond to the catalytic results obtained with the catalyst of 100-300 m size fraction, while the empty symbols correspond to those obtained with the catalyst of 10-20 μm size fraction. The arrows on the right indicate the thermodynamic equilibrium values at the respective temperature and pressure.
Figure 3:
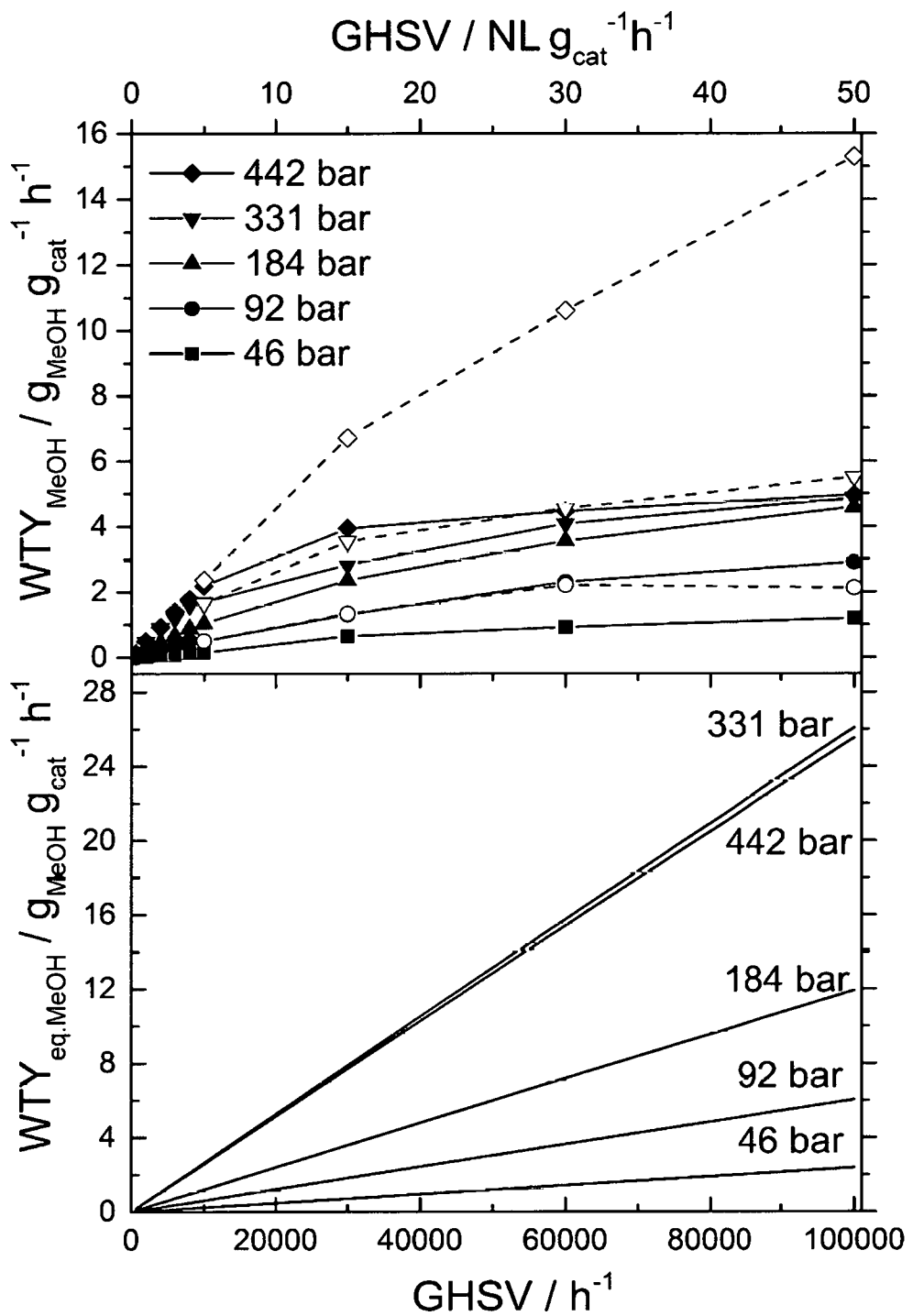
FIG. 3 is a graph showing (top) methanol weight time yield ($WTY_{MeOH}$) in high-pressure stoichiometric $CO_2$ hydrogenation at different GHSV conditions (650-100,000 $h^{-1}$, equivalent to 0.37-49.85 NL $g_{cat}^{-1}$ $h^{-1}$) at 280° C. (46 bar, 92 bar, 184 bar, and 442 bar) and at 260° C. (331 bar) using a commercial Cu/ZnO/$Al_2O_3$ catalyst. The filled symbols correspond to the catalytic results obtained with the catalyst of 100-300 μm size fraction, while the empty symbols correspond to those obtained with the catalyst of 10-20 μm size fraction, and (bottom) $WTY_{MeOH}$ at equilibrium conversion and selectivity at the different GHSVs at 280° C. (46 bar, 92 bar, 184 bar, and 442 bar) and at 260° C. (331 bar).

The reaction performance under the high-pressure conditions at the optimum temperature was further evaluated in a wide range of GHSV (650-100,000 $h^{-1}$, equivalent to 0.37-49.85 NL $g_{cat}^{-1}$ $h^{-1}$). FIG. 2 presents $CO_2$ conversion and methanol selectivity and FIG. 3 presents methanol yield as a function of GHSV at 46, 92, 184, 331, and 442 bar. In FIG. 2, equilibrium $CO_2$ conversion and methanol selectivity values are indicated. This section concerns the results using the catalyst particle of 100-300 μm in size (filled symbols in FIGS. 2 and 3).

What is striking from the dependence of methanol yield on GHSV (FIG. 2) is that there are reaction conditions giving high $CO_2$ conversion and methanol selectivity with methanol yield close to 1.0 $g_{MeOH}$ $g_{cat}^{-1}$ $h^{-1}$, which is generally considered to be an excellent yield. At 442 bar, the yield reached the value of 0.92 $g_{MeOH}$ $g_{cat}^{-1}$ $h^{-1}$ at 4,000 $h^{-1}$ with 88.5% $CO_2$ conversion and 97.2% methanol selectivity (Table 2). 0.89 $g_{MeOH}$ $g_{cat}^{-1}$ $h^{-1}$ was obtained at 331 bar also at 4,000 $h^{-1}$ with 83.3% and 96.8% methanol selectivity (Table 3). Similar methanol yield can be attained at lower pressure, but this requires increasing GHSV due to lower $CO_2$ conversion and methanol selectivity. For example, at 184 bar, 0.88 $g_{MeOH}$ $g_{cat}^{-1}$ $h^{-1}$ was obtained at 8,000 $h^{-1}$ with 47.0% $CO_2$ conversion and 84.8% methanol selectivity (Table 4). At 92 bar (shown for comparison with the invention), a high GHSV of 30,000 $h^{-1}$ was necessary (Table 5) to achieve 1.0 $g_{MeOH}$ $g_{cat}^{-1}$ $h^{-1}$ with poor $CO_2$ conversion (28.6%) and methanol selectivity (53.6%). At 46 bar, an even higher GHSV of 100,000 $h^{-1}$ was necessary (Table 6) to achieve 1.0 $g_{MeOH}$ $g_{cat}^{-1}$ $h^{-1}$ with poor $CO_2$ conversion (20.2%) and methanol selectivity (19.7%).

The reaction mechanisms of methanol synthesis in $CO_2$ hydrogenation, namely via $CO_2$ or CO, is widely debated (E. L. Kunkes, F. Studt, F. Abild-Pedersen, R. Schlogl, M. Behrens, J. Catal., 328 (2015) 43-48). In this Example, CO selectivity consistently increased (FIG. 2 and Tables 2-5) at higher GHSV. The results indicate that longer residence time may enhance methanol selectivity, and that methanol synthesis may proceed via CO produced by RWGS. The same conclusion had been drawn in over-stoichiometric $CO_2$ hydrogenation where excess hydrogen was used ($CO_2$:$H_2$=1:10) (A. Bansode, A. Urakawa, J. Catal., 309 (2014) 66-70).

In practice, high conversion and high methanol selectivity may not be the most critical performance indicator when unreacted $CO_2$, CO, and $H_2$ are efficiently recycled. Although larger volumetric flow (i.e. high GHSV) demands for higher energetic requirement for the recycling process due to low $CO_2$ conversion, such conditions can greatly improve methanol yield. This was demonstrated under the high GHSV conditions of this work (FIG. 3, filled symbols using 100-300 μm catalyst particles). At 100,000 $h^{-1}$ even at 92 bar, a very high yield of ca. 3 $g_{MeOH}$ $g_{cat}^{-1}$ $h^{-1}$ was achieved and overall excellent yields above 4.5 $g_{MeOH}$ $g_{cat}^{-1}$ $h^{-1}$ could be attained above 184 bar. Interestingly, the high-pressure benefit in $CO_2$ conversion was less pronounced at high GHSV using the catalyst of 100-300 μm in size, and the conversion values converged to roughly 20-30% at 100,000 $h^{-1}$ for all examined pressure conditions. In contrast, high-pressure advantage in methanol selectivity remained (70.0% at 331 bar and 47.7% at 92 bar). There, the reactivity features under high-pressure conditions have led to small differences in methanol yield between 184-442 bar, supporting that extremely productive methanol synthesis is possible at mildly high-pressure (e.g. 184 bar) when feed recycling is feasible.

TABLE 2

Effect of GHSV on $CO_2$ and $H_2$ conversions, product selectivity and yield using the Cu/ZnO/$Al_2O_3$ catalyst at a reactant pressure of 442 bar (reaction pressure of 480 bar), 280° C., and $CO_2$:$H_2$ = 1:3

| | Conv./% | | Sel./% | | | | WTY/mg$_{MeOH}$ $g_{cat}^{-1}$ $h^{-1}$ | | | |
| --- | --- | --- | --- | --- | --- | --- | --- | --- | --- | --- |
| GHSV/$h^{-1}$ | $CO_2$ | $H_2$ | CO | $CH_4$ | EtOH | MeOH | CO | $CH_4$ | EtOH | MeOH |
| 650 | 89.9 | 87.8 | 6.2 | 6.2 | 0.3 | 87.6 | 8.3 | 4.6 | 1.2 | 133.7 |
| 2000 | 90.7 | 86.5 | 3.9 | 1.4 | — | 94.8 | 17.4 | 3.3 | — | 487.6 |
| 4000 | 88.5 | 86.8 | 1.9 | 0.9 | — | 97.2 | 37.5 | 5.2 | — | 920.4 |
| 6000 | 88.0 | 84.3 | 3.0 | 0.5 | — | 96.5 | 61.0 | 3.4 | — | 1402.6 |
| 8000 | 86.1 | 84.2 | 5.5 | 0.4 | — | 94.1 | 88.9 | 3.6 | — | 1776.4 |
| 10000 | 84.7 | 81.9 | 6.6 | 0.4 | — | 93.1 | 135.1 | 4.1 | — | 2177.8 |
| 30000 | 61.3 | 59.0 | 18.3 | 0.0 | — | 81.7 | 708.3 | 0.0 | — | 3948.1 |
| 60000 | 45.1 | 41.1 | 39.7 | 0.0 | — | 60.3 | 2664.7 | 0.0 | — | 4465.9 |
| 100000 | 31.8 | 27.2 | 42.8 | 0.0 | — | 57.2 | 3427.5 | 0.0 | — | 4964.2 |

TABLE 3

Effect of GHSV on $CO_2$ and $H_2$ conversions, product selectivity and yield using the Cu/ZnO/$Al_2O_3$ catalyst at a reactant pressure of 331 bar (reaction pressure of 360 bar), 260° C., and $CO_2$:$H_2$ = 1:3

| | Conv./% | | Sel./% | | | | WTY/mg$_{MeOH}$ $g_{cat}^{-1}$ $h^{-1}$ | | | |
| --- | --- | --- | --- | --- | --- | --- | --- | --- | --- | --- |
| GHSV/$h^{-1}$ | $CO_2$ | $H_2$ | CO | $CH_4$ | EtOH | MeOH | CO | $CH_4$ | EtOH | MeOH |
| 650 | 89.0 | 85.0 | 1.4 | 0.7 | 0.1 | 97.8 | 1.9 | 0.6 | 0.9 | 154.5 |
| 2000 | 86.5 | 85.1 | 2.2 | 0.4 | — | 97.4 | 9.4 | 1.1 | — | 477.8 |

TABLE 3-continued

Effect of GHSV on $CO_2$ and $H_2$ conversions, product selectivity and yield using the $Cu/ZnO/Al_2O_3$ catalyst at a reactant pressure of 331 bar (reaction pressure of 360 bar), 260° C., and $CO_2:H_2 = 1:3$

| GHSV/$h^{-1}$ | Conv./% | | Sel./% | | | | WTY/$mg_{MeOH} g_{cat}^{-1} h^{-1}$ | | | |
|---|---|---|---|---|---|---|---|---|---|---|
| | $CO_2$ | $H_2$ | CO | $CH_4$ | EtOH | MeOH | CO | $CH_4$ | EtOH | MeOH |
| 4000 | 83.3 | 83.2 | 3.0 | 0.2 | — | 96.8 | 12.2 | 0.5 | — | 885.4 |
| 6000 | 74.8 | 72.3 | 3.9 | 0.1 | — | 96.0 | 14.5 | 0.2 | — | 1187.2 |
| 8000 | 69.5 | 66.8 | 4.3 | 0.1 | — | 95.5 | 14.8 | 0.3 | — | 1590.9 |
| 10000 | 61.0 | 58.8 | 6.1 | 0.1 | — | 93.7 | 97.0 | 1.3 | — | 1692.8 |
| 30000 | 40.2 | 37.6 | 13.9 | 0.0 | — | 86.2 | 397.8 | 0.0 | — | 2826.6 |
| 60000 | 33.2 | 27.9 | 23.8 | 0.1 | — | 76.1 | 564.0 | 0.7 | — | 4082.6 |
| 100000 | 25.3 | 20.4 | 30.0 | 0.0 | — | 70.0 | 541.5 | 0.2 | — | 4867.8 |

TABLE 4

Effect of GHSV on $CO_2$ and $H_2$ conversions, product selectivity and yield using the $Cu/ZnO/Al_2O_3$ catalyst at at a reactant pressure of 184 bar (reaction pressure of 200 bar), 280° C., and $CO_2:H_2 = 1:3$

| GHSV/$h^{-1}$ | Conv./% | | Sel./% | | | | WTY/$mg_{MeOH} g_{cat}^{-1} h^{-1}$ | | | |
|---|---|---|---|---|---|---|---|---|---|---|
| | $CO_2$ | $H_2$ | CO | $CH_4$ | EtOH | MeOH | CO | $CH_4$ | EtOH | MeOH |
| 650 | 37.3 | 33.3 | 7.0 | 1.7 | 0.1 | 91.0 | 4.1 | 0.5 | 0.9 | 60.2 |
| 2000 | 44.1 | 41.7 | 8.5 | 0.6 | — | 90.9 | 18.9 | 0.7 | — | 228.3 |
| 4000 | 47.1 | 43.5 | 11.9 | 0.3 | — | 87.8 | 55.3 | 0.8 | — | 460.4 |
| 6000 | 46.4 | 43.6 | 13.5 | 0.4 | — | 86.1 | 91.8 | 1.0 | — | 662.4 |
| 8000 | 47.0 | 44.4 | 15.1 | 0.1 | — | 84.8 | 142.4 | 0.0 | — | 876.9 |
| 10000 | 45.5 | 40.4 | 13.9 | 0.3 | — | 85.8 | 147.3 | 2.2 | — | 1031.6 |
| 30000 | 37.1 | 28.8 | 22.7 | 0.1 | — | 77.3 | 599.3 | 0.0 | — | 2352.5 |
| 60000 | 32.8 | 22.8 | 33.7 | 0.0 | — | 66.3 | 1610.6 | 0.0 | — | 3559.6 |
| 100000 | 26.6 | 15.2 | 36.3 | 0.0 | — | 63.7 | 2342.5 | 0.0 | — | 4592.6 |

TABLE 5

(comparative example) Effect of GHSV on $CO_2$ and $H_2$ conversions, product selectivity and yield using the $Cu/ZnO/Al_2O_3$ catalyst at a reactant pressure of 92 bar (reaction pressure of 100 bar), 280° C., and $CO_2:H_2 = 1:3$

| GHSV/$h^{-1}$ | Conv./% | | Sel./% | | | | WTY/$mg_{MeOH} g_{cat}^{-1} h^{-1}$ | | | |
|---|---|---|---|---|---|---|---|---|---|---|
| | $CO_2$ | $H_2$ | CO | $CH_4$ | EtOH | MeOH | CO | $CH_4$ | EtOH | MeOH |
| 650 | 32.3 | 23.6 | 78.1 | 8.6 | — | 13.0 | 39.4 | 2.5 | — | 7.4 |
| 2000 | 33.2 | 25.8 | 27.4 | 0.8 | — | 71.8 | 43.1 | 0.5 | — | 128.9 |
| 4000 | 32.9 | 26.7 | 26.3 | 0.4 | — | 73.3 | 82.5 | 0.8 | — | 261.7 |
| 6000 | 32.6 | 25.8 | 36.1 | 0.4 | — | 69.7 | 167.5 | 1.2 | — | 337.3 |
| 8000 | 30.9 | 27.6 | 26.4 | 0.4 | — | 64.9 | 169.9 | 1.6 | — | 537.5 |
| 10000 | 30.0 | 21.3 | 45.4 | 0.2 | — | 54.9 | 326.6 | 0.9 | — | 450.1 |
| 30000 | 28.6 | 22.8 | 49.8 | 0.4 | — | 53.6 | 1124.7 | 3.8 | — | 1293.7 |
| 60000 | 25.9 | 18.3 | 44.6 | 0.8 | — | 51.2 | 1635.9 | 17.6 | — | 2312.6 |
| 100000 | 22.4 | 13.7 | 52.3 | 0.6 | — | 47.7 | 2795.6 | 22.1 | — | 2892.6 |

TABLE 6

(comparative example) Effect of GHSV on $CO_2$ and $H_2$ conversions, product selectivity and yield using the $Cu/ZnO/Al_2O_3$ catalyst at a reactant pressure of 46 bar (reaction pressure of 50 bar), 280° C., and $CO_2:H_2 = 1:3$

| | Conv./% | | Sel./% | | | | $WTY/mg_{MeOH} \, g_{cat}^{-1} \, h^{-1}$ | | | |
|---|---|---|---|---|---|---|---|---|---|---|
| GHSV/$h^{-1}$ | $CO_2$ | $H_2$ | CO | $CH_4$ | EtOH | MeOH | CO | $CH_4$ | EtOH | MeOH |
| 650 | 21.4 | 12.7 | 93.6 | — | 0.0 | 6.4 | 30.66 | — | 0.0 | 2.4 |
| 2000 | 25.4 | 14.7 | 92.6 | — | 0.1 | 8.4 | 111.3 | — | 0.2 | 11.5 |
| 4000 | 24.3 | 14.3 | 73.6 | — | 0.2 | 26.3 | 169.8 | — | 0.9 | 69.4 |
| 6000 | 24.0 | 14.4 | 73.9 | — | 0.2 | 26.0 | 252.3 | — | 1.1 | 101.5 |
| 8000 | 23.8 | 14.1 | 75.4 | — | 0.2 | 24.5 | 340.0 | — | 1.4 | 126.5 |
| 10000 | 23.8 | 14.3 | 77.2 | — | 0.2 | 22.8 | 444.3 | — | 2.5 | 150.0 |
| 30000 | 25.1 | 11.2 | 76.8 | — | 0.2 | 22.3 | 2116.6 | — | 6.5 | 651.6 |
| 60000 | 24.0 | 11.0 | 70.1 | — | 0.2 | 23.3 | 2542.1 | — | 12.2 | 908.4 |
| 100000 | 20.2 | 10.0 | 80.3 | — | 0.2 | 19.7 | 4255.5 | — | 17.4 | 1191.1 |

Effect of Catalyst Particle Size

The same catalyst was prepared as described above, under the "experimental procedure" heading in this Example. However, instead of crushing and sieving the catalyst to a particle size of 100-300 µm, in this case the catalyst pellet was crushed and sieved to a particle size of 10-20 µm (10-20 microns). When the experiments described above that were carried out at reaction pressures of 100, 360 and 480 bar were repeated using the catalyst with a particle size of 10-20 µm, remarkable further improvements were obtained, as shown in the following tables of results and in FIGS. 2 and 3 (empty symbols). Particularly, at 442 bar methanol weight time yield was drastically improved compared to the case where the larger catalyst particle was employed. With the 10-20 µm catalyst particles, a very high weigh time yield as high as 15.3 $g_{MeOH} \, g_{cat}^{-1}$ could be attained at 100,000 $h^{-1}$. This improvement is due to the efficient utilization of active catalyst component (i.e. larger accessible diffusion layer) due to the smaller sizing of molecular diffusional length under the conditions where product condensation takes place thus diffusion processes are highly limited.

TABLE 7

(comparative example) Effect of GHSV on $CO_2$ and $H_2$ conversions, product selectivity and yield using the $Cu/ZnO/Al_2O_3$ catalyst, with a particle size of 10-20 microns, at a reactant pressure of 92 bar (reaction pressure of 100 bar), 280° C., and $CO_2:H_2 = 1:3$

| | Conv./% | | Sel./% | | | | $WTY/mg_{MeOH} \cdot gcat^{-1} \cdot h^{-1}$ | | | |
|---|---|---|---|---|---|---|---|---|---|---|
| GHSV/$h^{-1}$ | $CO_2$ | $H_2$ | CO | $CH_4$ | EtOH | MeOH | CO | $CH_4$ | EtOH | MeOH |
| 10000 | 34.1 | 27.4 | 46.5 | 0.0 | 0.0 | 53.5 | 382.6 | 0.0 | 0.0 | 503.7 |
| 30000 | 29.3 | 21.0 | 45.1 | 0.0 | 0.0 | 52.5 | 958.4 | 0.0 | 0.0 | 1331.1 |
| 60000 | 25.1 | 16.5 | 51.9 | 0.0 | 0.0 | 48.1 | 1887.6 | 0.0 | 0.0 | 2003.2 |
| 100000 | 25.9 | 17.2 | 36.8 | 0.0 | 0.0 | 63.2 | 2262.4 | 0.0 | 0.0 | 4449.5 |

TABLE 8

Effect of GHSV on $CO_2$ and $H_2$ conversions, product selectivity and yield using the $Cu/ZnO/Al_2O_3$ catalyst, with a particle size of 10-20 microns, at a reactant pressure of 331 bar (reaction pressure of 360 bar), 260° C., and $CO_2:H_2 = 1:3$

| | Conv./% | | Sel./% | | | | $WTY/mg_{MeOH} \cdot gcat^{-1} \cdot h^{-1}$ | | | |
|---|---|---|---|---|---|---|---|---|---|---|
| GHSV/$h^{-1}$ | $CO_2$ | $H_2$ | CO | $CH_4$ | EtOH | MeOH | CO | $CH_4$ | EtOH | MeOH |
| 10000 | 63.7 | 57.2 | 6.5 | 0.0 | 0.0 | 93.5 | 100.1 | 0.0 | 0.0 | 1644.8 |
| 30000 | 46.4 | 38.2 | 11.9 | 0.0 | 0.0 | 88.1 | 418.4 | 0.0 | 0.0 | 3545.3 |
| 60000 | 33.8 | 25.8 | 18.7 | 0.0 | 0.0 | 81.3 | 912.6 | 0.0 | 0.0 | 4545.1 |
| 100000 | 27.2 | 22.4 | 25.0 | 0.0 | 0.0 | 75.0 | 1606.1 | 0.0 | 0.0 | 5513.5 |

TABLE 9

Effect of GHSV on $CO_2$ and $H_2$ conversions, product selectivity and yield using the $Cu/ZnO/Al_2O_3$ catalyst, with a particle size of 10-20 microns, at a reactant pressure of 442 bar (reaction pressure of 480 bar), 280° C., and $CO_2:H_2$ - 1:3

| GHSV/h$^{-1}$ | Conv./% | | Sel./% | | | | WTY/mg$_{MeOH}$·gcat$^{-1}$·h$^{-1}$ | | | |
|---|---|---|---|---|---|---|---|---|---|---|
| | $CO_2$ | $H_2$ | CO | $CH_4$ | EtOH | MeOH | CO | $CH_4$ | EtOH | MeOH |
| 10000 | 87.7 | 83.8 | 2.2 | 0.2 | 0.0 | 97.6 | 47.3 | 2.1 | 0.0 | 2364.8 |
| 30000 | 80.0 | 73.9 | 3.2 | 0.1 | 0.0 | 96.7 | 196.8 | 1.6 | 0.0 | 6714.8 |
| 60000 | 67.9 | 61.5 | 10.0 | 0.0 | 0.0 | 93.9 | 601.2 | 0.8 | 0.0 | 10554.7 |
| 100000 | 65.31 | 58.69 | 7.9 | 0.1 | 0.0 | 91.9 | 1242.8 | 12.5 | 0.0 | 15253.7 |

Example 2—Stoichiometric $CO_2$ Hydrogenation to Methanol Using Precipitated Cu/Zn Catalyst 1. Catalyst Synthesis 300 mL of pure water (HPLC grade) were added to a 1 L round bottom flask placed in a heating mantle. A solution of metal nitrates 0.5 M [$(Cu(NO_3)_2$ and $Zn(NO_3)_2$ Cu/Zn ratio: 70/30) was pumped at 2 mL/min into a stirred and pre-heated (60° C.) glass reactor. Simultaneously, a solution of $(NH_4)HCO_3$ (3 M) was pumped at a controlled speed in order to maintain the pH between 6.4 and 6.6. After full addition of the metal nitrate solution, the base flow was stopped and the system was left under stirring for 6 h. The resulting solid was filtered in a Büchner funnel, and left drying overnight at 60° C. Finally, the solid was calcined at 400° C. for 2 h using a heating ramp of 2° C./min.

2. Catalyst Characterisation

The pre-calcined coprecipitated catalyst is mainly formed by zincian malachite and aurichalcite. After calcination, the decomposition of the hydroxycarbonates took place, leaving only CuO and ZnO in the catalyst. The crystallite size of both oxides is around 7 nm as determined by XRD. After reduction (25 mL/min of 10% $H_2$/90% $N_2$ at 300° C. for 2 h), the Cu surface area of the resulting material was 23 m$^2$/g (Table 10).

TABLE 10

Further characterization of the coprecipitated catalysts

| Cu surface Area ($S_{Cu}$) | Metal content (wt %) | | Crystallite sizes * (nm) | | Reducibility |
|---|---|---|---|---|---|
| m$^2$/g | CuO | ZnO | CuO | ZnO | (%) |
| 23 | 74.9 | 25.1 | 7 | 7 | 86 |

* Crystallite sized calculated by Scherrer equation

3. Catalytic Activity

The stoichiometric $CO_2$ hydrogenation ($CO_2:H_2$=1:3) to methanol was performed at 331 and 442 bar at 10,000 h$^{-1}$ using the catalyst shaped in pellets of 100-300 μm size. The methanol weight-time yield (WTY) was above 1.2 g$_{MeOH}$ g$_{cat}$$^{-1}$ h$^{-1}$ with 52% $CO_2$ conversion and 84% methanol selectivity at 331 bar at 280° C. The same level of WTY (above 1.2 g$_{MeOH}$ g$_{cat}$$^{-1}$ h$^{-1}$) was also obtained at 442 bar at 300° C. with 56% $CO_2$ conversion and 92% methanol selectivity.

What is claimed is:

1. A process for producing methanol, which process comprises contacting $H_2$ and $CO_2$ with a solid catalyst, at a temperature of from 200° C. to 300° C. and at a reactant pressure of from 150 bar to 500 bar, which reactant pressure is the sum of the partial pressures of the $H_2$ and the $CO_2$, wherein said contacting comprises passing the $H_2$ and $CO_2$ over the solid catalyst at a space velocity of from 5,000 h$^{-1}$ to 50,000 h$^{-1}$ and wherein:
   the molar ratio of the $H_2$ to the $CO_2$ is x:1.0, wherein x is from 2.5 to 3.5; and
   the catalyst comprises 63.5 weight % of CuO, 24.7 weight % ZnO, 10.1 weight % Al2O3, and 1.3 weight % MgO, wherein the catalyst has a specific copper surface area ($S_{Cu}$) of at least 15 m$^2$/g-catalyst.

2. A process for producing methanol, which process comprises contacting $H_2$ and $CO_2$ with a solid catalyst, at a temperature of from 200° C. to 300° C. and at a reactant pressure of from 150 bar to 500 bar, which reactant pressure is the sum of the partial pressures of the $H_2$ and the $CO_2$, wherein said contacting comprises passing the $H_2$ and $CO_2$ over the solid catalyst at a space velocity of from 5,000 h$^{-1}$ to 50,000 h$^{-1}$ and wherein:
   the molar ratio of the $H_2$ to the $CO_2$ is x:1.0, wherein x is from 2.5 to 3.5; and
   the catalyst comprises (i) from 63% to 68% by weight CuO, (ii) from 22% to 26% by weight ZnO, (iii) from 8% to 12% by weight $Al_2O_3$, and (iv) from 1% to 2% by weight MgO, wherein the catalyst has a specific copper surface area ($S_{Cu}$) of at least 15 m$^2$/g-catalyst.

3. The process according to claim 2 wherein the catalyst comprises (i) from 63% to 66% by weight CuO, (ii) from 22% to 25% by weight ZnO, (iii) from 9% to 11% by weight $Al_2O_3$, and (iv) from 1% to 2% by weight MgO.

4. The process according to claim 2 wherein the catalyst comprises (i) from 63% to 65% by weight CuO, (ii) from 22% to 25% by weight ZnO, (iii) from 9% to 11% by weight $Al_2O_3$, and (iv) from 0.9% to 1.7% by weight MgO.

* * * * *